United States Patent
Strober et al.

(10) Patent No.: US 7,531,352 B2
(45) Date of Patent: May 12, 2009

(54) INDUCIBLE PLASMID VECTOR ENCODING TGF-β AND USE THEREOF

(75) Inventors: Warren Strober, Bethesda, MD (US); Kazuhiko Nakamura, Fukuoka (JP); Atsushi Kitani, Rockville, MD (US); Ivan J. Fuss, Jr., Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 1070 days.

(21) Appl. No.: 10/258,109

(22) PCT Filed: Apr. 20, 2001

(86) PCT No.: PCT/US01/12980

§ 371 (c)(1), (2), (4) Date: Jun. 30, 2003

(87) PCT Pub. No.: WO01/81404

PCT Pub. Date: Nov. 1, 2001

(65) Prior Publication Data

US 2006/0234964 A1  Oct. 19, 2006

Related U.S. Application Data

(60) Provisional application No. 60/199,041, filed on Apr. 20, 2000.

(51) Int. Cl.
*C12N 15/00* (2006.01)
*C12N 5/00* (2006.01)
*C12N 5/02* (2006.01)

(52) U.S. Cl. ..................... 435/320.1; 435/325
(58) Field of Classification Search ............. 435/320.1, 435/325
See application file for complete search history.

(56) References Cited

U.S. PATENT DOCUMENTS 5,958,403 A    9/1999   Strom et al. ............. 424/93.21

OTHER PUBLICATIONS

Kitani et al., 2000, J. Exp. Med. 192:41-52.*
O'Brien (Gene, 1997, Gene, vol. 184, p. 115-120.*
Samuel (EMBO, 1992, vol. 11, p. 1599-1605).*
Kulkin (J. Clin. Invest, 1998, vol. 102, p. 438).*
Prud'homme, J. Autoimmunity, 2000, vol. 14, p. 23-42).*
Giladi (E. J. Gastroenterol. Hepatol., 1995, vol. 7, p. 341-347).*
Wells (Transgenic Res. 1999, vol. 8, p. 371-381).*
Sturtz (Gene, Oct. 23, 1998, vol. 221, No. 2, p. 279-285).*
Gould (Gene Therapy, 2000, vol. 7, p. 2061-2070).*
Yu (Cancer Res., 1996, vol. 56, p. 5423-5427).*
A-Mohammadi (Gene Therapy, 1998, vol. 5, p. 76-84).*
A. Kitani et al., *J. Exp. Med.*, 192(1):41-52 (2000).
N. Kuklin et al., *J. Clin. Invest.*, 102(2):438-444 (1998).
C. Huang et al., *Molecular Medicine*, 5:129-137 (1999).
E. Giladi et al., *Eur. J. Gastroent. Hepatol.*, 7(4):341-347 (1995).
S. Samuel et al., *Embo. J.*, 11(4):1599-1605 (1992).

* cited by examiner

*Primary Examiner*—Michael C. Wilson
(74) *Attorney, Agent, or Firm*—Edwards Angell Palmer & Dodge LLP; Peter F. Corless; Christine C. O'Day

(57) ABSTRACT

The present invention provides alternatives to traditional drug and surgical treatments for IBD. In particular, the present invention provides compositions and methods for the treatment of autoimmune diseases such as IBD in humans using TGF-β therapy. The compositions of the present invention provide vectors containing TGF-β under the control of an inducible promoter. In particularly preferred embodiments, the present invention provides regulated plasmid constructs capable of inducing TGF-β production. In preferred embodiments, the methods of the present invention utilize the vectors described for assaying the expression of a gene in a cell. In some preferred embodiments, the methods of the present invention utilize the administration of TGF-β containing vectors to treat IBD. In alternative preferred embodiments, the present invention provides methods and compositions for the induction of high-level interleukin (e.g., IL-10) production.

8 Claims, 13 Drawing Sheets

FIGURE 1

```
      BglII KpnI    1
   1 AGATCTGGTACCGAG ATG GCG CCT TCG GGG CTG CGG CTC TTG CCG CTG CTG CTG CCG CTG CTG TGG CTG CTA GTG CTG ACG CCT GGC CGG CCG                              25XmaIII
                    Met Ala Pro Ser Gly Leu Arg Leu Leu Pro Leu Leu Leu Pro Leu Leu Trp Leu Leu Val Leu Thr Pro Gly Arg Pro
         XmaIII        ←
  94 GCC GCC GGA CTG TCC ACC TGC AAG ACC ATC GAC ATG GAG CTG GTG AAG CGG AAG CGC ATC GAG GCC ATT CGC GGC CAG ATT CTG TCC AAG      HindIII
     Ala Ala Gly Leu Ser Thr Cys Lys Thr Ile Asp Met Glu Leu Val Lys Arg Lys Arg Ile Glu Ala Ile Arg Gly Gln Ile Leu Ser Lys
                                                                        75
 184 CTT CGG CTC GCC AGC CCC CCG AGC CAG GGG GAC GTG CCG CCC GGC CCG CTG CCT GAG GCC GTA CTG GCT CTT TAC AAC AGT ACC CGC GAC
     Leu Arg Leu Ala Ser Pro Pro Ser Gln Gly Asp Val Pro Pro Gly Pro Leu Pro Glu Ala Val Leu Ala Leu Tyr Asn Ser Thr Arg Asp
                                                100
 274 CGG GTA GCC GGG GAA AGT GTC GAA CCG GAG CCC GAG CCA GAG GCG GAC TAC TAC GCC AAG GAG GTC ACC CGC GTG CTA ATG GTG GAA AGC
     Arg Val Ala Gly Glu Ser Val Glu Pro Glu Pro Glu Ala Asp Tyr Tyr Ala Lys Glu Val Thr Arg Val Leu Met Val Glu Ser
                                125
 364 GGC AAC CAA ATC TAT GAT AAA TTC AAG GGC ACC CCC CAC AGC TTA TAT ATG CTG TTC AAC ACG TCG GAG CTC CGG GAA GCG GTG CCG GAA     SstI
     Gly Asn Gln Ile Tyr Asp Lys Phe Lys Gly Thr Pro His Ser Leu Tyr Met Leu Phe Asn Thr Ser Glu Leu Arg Glu Ala Val Pro Glu
                150
 454 CCT GTA TTG CTC TCT CGG GCA GAG CTG CGC CTG CTG AGG CTC AAG TTA AAA GTG GAG CAG CAC GTG GAG CTA TAC CAG AAA TAC AGC AAT            175
     Pro Val Leu Leu Ser Arg Ala Glu Leu Arg Leu Leu Arg Leu Lys Leu Lys Val Glu Gln His Val Glu Leu Tyr Gln Lys Tyr Ser Asn
                                                         200
 544 GAT TCC TGG CGC TAC CTC AGC AAC CGG CTG CTG GCC CCC AGT GAC TCA CCG GAG TGG CTG TCC TTT GAT GTC ACC GGA GTT GTG CGG CAG
     Asp Ser Trp Arg Tyr Leu Ser Asn Arg Leu Leu Ala Pro Ser Asp Ser Pro Glu Trp Leu Ser Phe Asp Val Thr Gly Val Val Arg Gln
                                          225
  ,4 TGG CTG ACC CGC AGA GAG GCT ATA GAG GGT TTT CGC CTC AGT GCC CAC TCT TCC TCT GAC AGC AAA GAT AAC ACA CTC CAC GTG GAA ATT
     Trp Leu Thr Arg Arg Glu Ala Ile Glu Gly Phe Arg Leu Ser Ala His Ser Ser Ser Asp Ser Lys Asp Asn Thr Leu His Val Glu Ile
                                                     250
 724 AAC GGG TTC AAT TCT GGC CGC CGG GGT GAC CTG GCC ACC ATT CAC GGC ATG AAC CGG CCC TTC CTG CTC CTC ATG GCC ACC CCG CTG GAG
     Asn Gly Phe Asn Ser Gly Arg Arg Gly Asp Leu Ala Thr Ile His Gly Met Asn Arg Pro Phe Leu Leu Leu Met Ala Thr Pro Leu Glu
                                       275
 814 AGG GCC CAG CAC CTG CAC AGC TCC CGG CAC CGC CGA GCC CTG GAT ACC AAC TAC TGC TTC AGC TCC ACG GAG AAG AAC TGC TGC GTG CGG
     Arg Ala Gln His Leu His Ser Ser Arg His Arg Arg Ala Leu Asp Thr Asn Tyr Cys Phe Ser Ser Thr Glu Lys Asn Cys Cys Val Arg
                                 300                                                                                    325
 904 CAG CTC TAC ATT GAC TTC CGG AAG GAC CTG GGC TGG AAG TGG ATT CAT GAA CCC AAG GGC TAC CAT GCC AAT TTC TGC CTG GGG CCC TGT
     Gln Leu Tyr Ile Asp Phe Arg Lys Asp Leu Gly Trp Lys Trp Ile His Glu Pro Lys Gly Tyr His Ala Asn Phe Cys Leu Gly Pro Cys
                                                                                                        SmaI    350
 994 CCC TAC ATC TGG AGC CTA GAC ACT CAG TAC AGC AAG GTC CTG GCT CTG TAC AAC CAG CAC AAC CCG GGC GCG GCG CCG TGC TGC
     Pro Tyr Ile Trp Ser Leu Asp Thr Gln Tyr Ser Lys Val Leu Ala Leu Tyr Asn Gln His Asn Pro Gly Ala Ser Ala Ala Pro Cys Cys
                                                        375         PvuII
1084 GTG CCG CAG GCG CTG GAG CCA CTG CCC ATC GTG TAC TAC GTG GGC CGC AAG CCC AAG GTG GAG CAG CTC TCC AAC ATG ATC GTG CGT TCC
     Val Pro Gln Ala Leu Glu Pro Leu Pro Ile Val Tyr Tyr Val Gly Arg Lys Pro Lys Val Glu Gln Leu Ser Asn Met Ile Val Arg Ser
                  390PvuII
1174 TGC AAG TGC AGC TGA GCCCCGCCCCGCCCACAGCCCCGCCCACCCGGCAGGCCCGGCCCCACCCCCGCCCGCCTCACCGGGCCTCTATTTAAGGACATCGTGCCCCAAGCCCAC
     Cys Lys Cys Ser ...
                    KpnI  BglII
1290 TGGGATCGATTAAAGGTGGAGAGAGGAGGTACCAGATCT
```

INDUCIBLE PLASMID VECTOR ENCODING TGF-β AND USE THEREOF

The present application claims priority to U.S. Provisional Patent Application Ser. No. 60/199,041, filed on Apr. 20, 2000.

FIELD OF THE INVENTION

The present invention provides compositions comprising nucleic acid constructs encoding TGF-β for the treatment of autoimmune diseases (e.g., inflammatory bowel disease). Furthermore, the invention provides methods for the use of these compositions for the treatment of inflammatory bowel disease. In particularly preferred embodiments, the present invention provides regulated plasmid constructs capable of inducing TGF-β production.

BACKGROUND OF THE INVENTION

The immune system serves to protect the host from invasion by foreign organisms by distinguishing "self" from "nonself." When the immune system recognizes host antigens (autoantigens) as foreign, autoimmune disease results, causing tissue destruction and functional impairment (See, e.g. Tlaskalova-Hogenova, et al., Folia Microbiol., 43:545-550 [1998]). One example of an autoimmune disease is Inflammatory Bowel Disease ("IBD").

IBD is defined by chronic, relapsing intestinal inflammation of obscure origin. IBD includes two distinct disorders, namely, Crohn's disease and ulcerative colitis (UC). Both diseases appear to result from the unrestrained activation of an inflammatory response in the intestine. This inflammatory cascade is thought to be perpetuated through the actions of proinflammatory cytokines and activation of selective lymphocyte subsets. In patients with IBD, ulcers and inflammation of the inner lining of the intestines lead to such symptoms as abdominal pain, diarrhea, and rectal bleeding. Ulcerative colitis occurs in the large intestine, while in Crohn's disease, the disease can involve the entire gastrointestinal (GI) tract as well as the small and large intestines. For most patients, IBD is a chronic condition with symptoms lasting for months to years. It is most common in young adults, but can occur at any age. It is found worldwide, but is most common in industrialized countries such as the United States, England, and northern Europe. The clinical symptoms of IBD are intermittent rectal bleeding, crampy abdominal pain, weight loss and diarrhea Diagnosis of IBD is often based on the clinical symptoms and/or the use of a barium enema, but direct visualization (sigmoidoscopy or colonoscopy) is the most accurate test. Protracted IBD is a risk factor for colon cancer, and treatment of IBD can involve medications and surgery.

Some patients with UC only have disease in the rectum (proctitis). Others with UC have disease limited to the rectum and the adjacent left colon (proctosigmoiditis). Yet others have UC of the entire colon (universal IBD). Symptoms of UC are generally more severe with more extensive disease (e.g. where a larger portion of the colon is involved with disease).

The prognosis for patients with disease limited to the rectum (proctitis) or UC limited to the end of the left colon (proctosigmoiditis) is better than that of patients whose disease affects the entire colon. Brief periodic treatments using oral medications or enemas may be sufficient. In those with more extensive disease, blood loss from the inflamed intestines can lead to anemia, and may require treatment with iron supplements or even blood transfusions. Rarely, when the inflammation becomes very severe, the colon can acutely dilate to a large size. This condition is called "toxic megacolon." Patients with toxic megacolon are extremely ill with fever, abdominal pain and distention, dehydration, and malnutrition. Unless the patient improves rapidly with medication, surgery is usually necessary to prevent colon rupture.

Crohn's disease can occur in all regions of the gastrointestinal tract. Intestinal obstruction due to inflammation and fibrosis occurs in a large number of patients. Abscesses and fistula formation are frequent complications of Crohn's disease. Disease progression consequences include intravenous feeding, surgery and colostomy.

Colon cancer is a known complication of chronic IBD. It is increasingly common in those patients who have had extensive IBD over many years. The risk for cancer begins to rise significantly after eight to ten years of IBD.

Several treatments exist for IBD, including medication, nutritional therapy, and surgery (See e.g., Evans and Ciclitira, The Practitioner, 243:307-314 [1999]; Rampton, Brit. Med. J., 319:1480-5 [1999]; and Stein and Hanauer, Gastroenterol. Clin., 28: 297-321 [1999]). Patients who wish to avoid corticosteroids (especially children) are often treated with a liquid formula diet. The diet is given as the only nutritional source for 4-6 weeks. However, the usefulness of dietary treatment is limited by the expense of formulations and the high rate of relapse following discontinuation.

The most commonly used medications to treat IBD are anti-inflammatory drugs such as the salicylates. Examples of salicylates include sulfasalazine, and the newer drug mesalazine. Mesalazine is given orally in high doses for maximal therapeutic benefit. The salicylate preparations have been effective in treating mild to moderate disease. However, these drugs, including newer medications such as mesalazine are not without side effects such as headache, nausea, diarrhea, pancreatitis, as well as blood dyscrasias and interstitial nephritis in some patients. Nonetheless, these drugs can also decrease the frequency of disease flares when the medications are taken on a prolonged basis. However, a four month course of high dose mesalazine induced remission in only 40% of patients with mildly active Crohn's disease (Rampton, Brit. Med. J., 319:1480-5 [1999]).

Corticosteroids are more potent and faster-acting than salicylates in the treatment of IBD, but potentially serious side effects limit the use of corticosteroids to these patients with more severe disease. Side effects of corticosteroids usually occur with long term use. They include thinning of the bone and skin, infections, diabetes, muscle wasting, rounding of faces, psychiatric disturbances, and, on rare occasions, destruction of hip joints.

In IBD patients that do not respond to salicylates or corticosteroids, medications that suppress the immune system are used. Examples of immunosuppressants include azathioprine and 6-mercaptopurine. Immunosuppressants used in this situation help to control IBD and allow gradual reduction or elimination of corticosteroids. However, immunosuppressants render the patient immuno-compromised and susceptible to many other diseases.

Patients who fail to respond to dietary or drug therapy require surgical resection. However, surgery is often not curative and 50% of patients require additional surgery. There remains a great need for agents capable of preventing and treating IBD. In particular, agents suitable for administration in a cost-effective and timely fashion, with a minimum of adverse side effects are needed. The present invention, as described below, provides treatments for IBD that solve many of the problems of the currently available treatments.

DESCRIPTION OF THE FIGURES

FIG. 1 shows the sequence of SEQ ID NO:1 used in some embodiments of the present invention. SEQ ID NO:2 (i.e., the amino acid sequence) is also shown.

FIG. 3, Panel A shows the plasmid vector pTet-CMV-TGF-β1 (i.e., pTet-on-TGF-β1) used in some embodiments of the present invention, while Panel B shows the results of Western blot analysis of COS7 cells transfected with pTet-CMV-TGF-β1 or mock pTet-on.

SUMMARY OF THE INVENTION

Figure 2:
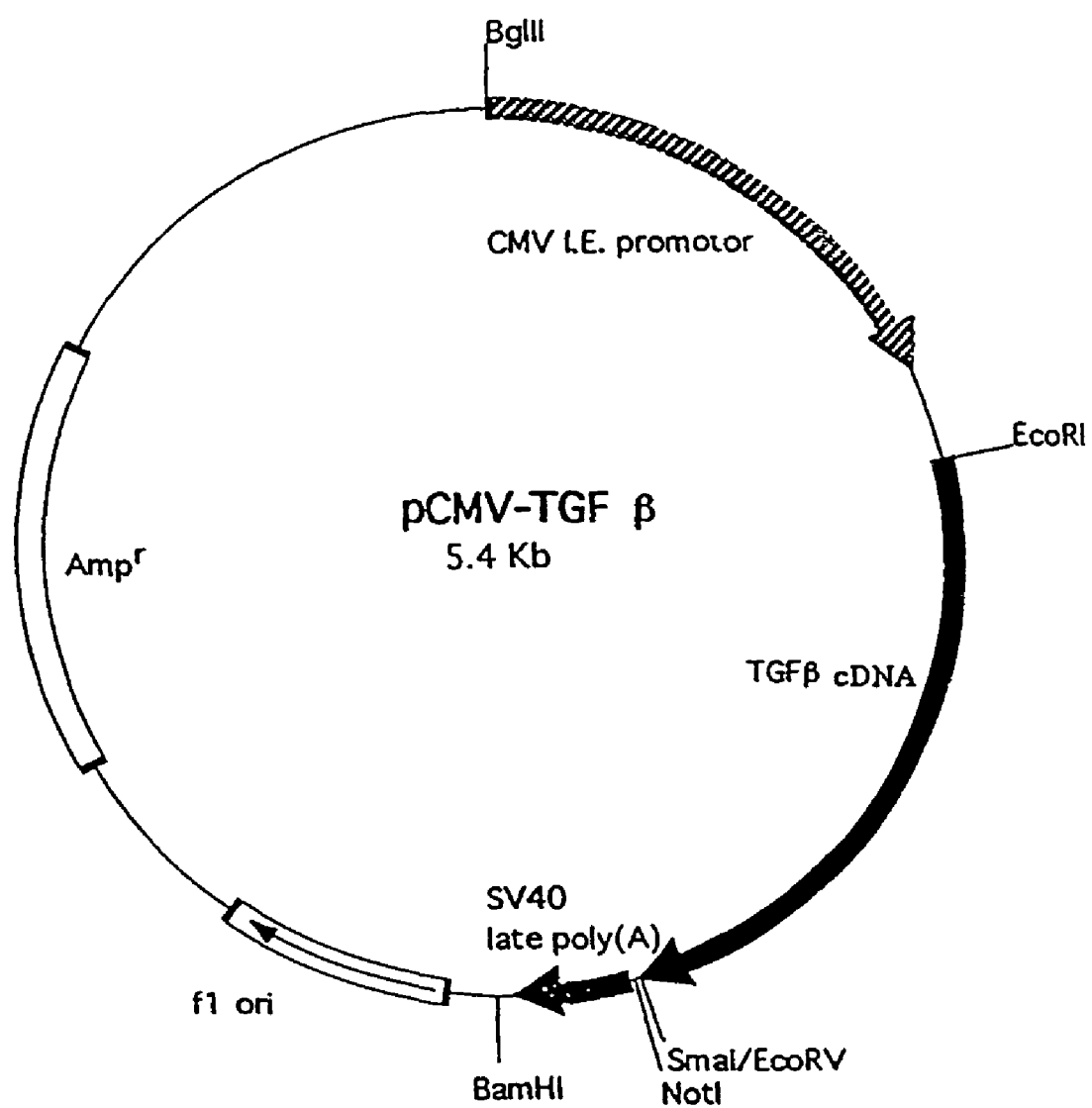
FIG. 2 shows the plasmid vector pCMV-TGF-β1 used in some embodiments of the present invention.

The present invention provides compositions comprising nucleic acid constructs encoding transforming growth factor beta (i.e., "TGF-β") for the treatment of autoimmune diseases (e.g., inflammatory bowel disease). In particularly preferred embodiments, constructs comprising TGF-β1 are used. Furthermore, the invention provides methods for the use of these compositions for the treatment of inflammatory bowel disease. In particularly preferred embodiments, the present invention provides regulated plasmid constructs capable of inducing TGF-β production. In further particularly preferred embodiments, the present invention provides regulated plasmid constructs capable of inducing TGF-β1 production. The present invention further provides methods and compositions for the induction of high-level IL-10 responses, thereby providing improved means for down-regulating inflammation. In addition, the present invention provides compositions and methods to induce TGF-β (e.g., TGF-β1) production without concomitant induction of fibrosis. Indeed, the present invention provides means to block fibrosis, such as that induced by bleomycin, a well-known fibrosis-inducing agent.

The present invention provides composition comprising a vector, wherein the vector further comprises a gene encoding a regulatory transcription factor which is under the control of a first promoter, and a nucleic acid sequence of SEQ ID NO:1 which is under the control of a second promoter which is inducible. In some embodiments, the first promoter comprises a CMV promoter. In yet other embodiments, the second, inducible promoter comprises a TRE-CMV promoter. The present invention also comprises a cell transfected with the vector described herein.

The present invention also provides vectors wherein the vectors further comprise a gene encoding a regulatory transcription factor which is under the control of a first promoter, and a nucleic acid sequence selected from the group consisting of SEQ ID NO:1, variants of SEQ ID NO:1, and homologs of SEQ ID NO:1, wherein the nucleic acid is under the control of a second, inducible promoter. In some embodiments, the first promoter comprises a CMV promoter. In other embodiments, the second, inducible promoter comprises a TRE-CMV promoter. The present invention also comprises a cell transfected with the vector described herein.

The present invention further provides methods for expression of a polypeptide comprising: a) providing: a vector comprising a gene encoding a regulatory transcription factor which is under the control of a first promoter, and a nucleic acid sequence selected from the group consisting of SEQ ID NO:1, variants of SEQ ID NO:1, and homologs of SEQ ID NO:1, wherein the nucleic acid sequence is under the control of a second, inducible promoter, and a cell; and b) transfecting the cell with the vector under conditions such that expression of the polypeptide encoded by the nucleic acid sequence results. In some embodiments, the first promoter comprises a CMV promoter. In other embodiments, the second inducible promoter comprises a TRE-CMV promoter. In yet another embodiment, the cell is part of a host.

The present invention also provides a method for expression of a polypeptide comprising: a) providing a vector comprising a gene encoding a regulatory transcription factor which is under the control of a first promoter, and a nucleic acid sequence selected from the group consisting of SEQ ID NO:1, variants of SEQ ID NO:1, and homologs of SEQ ID NO:1, wherein the nucleic acid sequence is under the control of a second inducible promoter; a host; and a delivery system; and b) delivering the vector to the host using the delivery system under conditions such that expression of the polypeptide encoded by the nucleic acid sequence results. In some embodiments, the first promoter comprises a CMV promoter. In other embodiment, the second inducible promoter comprises a TRE-CMV promoter. In still other embodiments, the delivery system comprises intranasal administration. In yet other embodiments, the host is suspected of having an autoimmune disease. In some embodiments, the autoimmune disease is IBD. In other embodiments, the delivery of the vector results in substantial elimination of symptoms of the autoimmune disease.

The present invention also provides compositions comprising a vector, wherein the vector further comprises a gene encoding a regulatory transcription factor under the control of a first promoter, and a gene encoding a TGF-β polypeptide under the control of a second promoter, wherein the second promoter is inducible. In some embodiments, the second promoter comprises a TRE-CMV promoter. In still other variations of this embodiment, the present invention provides a host cell which contains this vector. In yet further embodiments, the transforming growth factor beta polypeptide is selected from the group consisting of TGF-β1, TGF-β2, TGF-β3, variants of TGF-β1, TGF-β2, and TGF-β3, and homologs of TGF-β1, TGF-β2, and TGF-β3. In variations of this embodiment, the second promoter comprises a TRE-CMV promoter. In still other variations of this embodiment, the present invention provides a host cell which contains this vector. In yet other embodiments, the gene encoding a TGF-β polypeptide encodes a variant of TGF-β1, and has the nucleic acid sequence set forth in SEQ ID NO:1. In variations of this embodiment, the second promoter comprises a TRE-CMV promoter. In still other variations of this embodiment, the present invention provides a host cell which contains this vector.

The present invention also provides methods for the expression of a polypeptide encoding a TGF-β polypeptide comprising the steps of providing a vector, wherein the vector comprises a gene encoding a regulatory transcription factor under the control of a first promoter, and a gene encoding a TGF-β polypeptide under the control of a second promoter, wherein the second promoter is inducible, a host, and a delivery system; and delivering the vector to the host using the delivery system under conditions such that expression of the gene encoding a TGF-β polypeptide occurs. In some embodiments, the second promoter comprises a TRE-CMV promoter. In other embodiments, the gene encoding a TGF-β polypeptide encodes a variant of TGF-β1, and has the nucleic acid sequence set forth in SEQ ID NO:1. In still further embodiments, the TGF-β polypeptide is selected from the group consisting of TGF-β1, TGF-β2, TGF-β3, variants of TGF-β1, TGF-β2, and TGF-β3, and homologs of TGF-β1, TGF-β2, and TGF-β3. In variations of these embodiments, the second promoter comprises a TRE-CMV promoter. In still other variations of these embodiments, the gene encoding a TGF-β polypeptide encodes a variant of TGF-β1 and has the nucleic acid sequence set forth in SEQ ID NO:1. In yet other variations of the embodiments in which the gene encoding a TGF-β polypeptide encodes a variant of TGF-β1, and has the nucleic acid sequence set forth in SEQ ID NO:1, the second promoter comprises a TRE-CMV promoter.

Definitions

To facilitate an understanding of the present invention, a number of terms and phrases are defined below:

As used herein, the term "nucleic acid sequence" refers to an oligonucleotide or polynucleotide, and fragments or portions thereof, and to DNA or RNA of genomic or synthetic origin that may be single- or double-stranded, and represent the sense or antisense strand. The term encompasses sequences that include any of the known base analogues of DNA and RNA.

As used herein, the term "promoter" refers to short arrays of DNA sequences that interact specifically with cellular proteins involved in transcription (Maniatis et al., Science 236: 1237 [1987]). Promoter elements have been isolated from a variety of prokaryotic, eukaryotic, and viral sources. The selection of a particular promoter depends on what cell type is to be used to express the protein of interest. The term "inducible promoter" refers to a promoter element that is activated by a specific compound (e.g., doxycycline).

As used herein, the term "gene" refers to a nucleic acid (e.g. DNA) sequence that comprises coding sequences necessary for the production of a polypeptide or precursor (e.g., TGF-β. The polypeptide can be encoded by a full length coding sequence or by any portion of the coding sequence so long as the desired activity or functional properties (e.g., therapeutic action, ligand binding, signal transduction, etc.) of the full-length polypeptide or polypeptide fragment are retained. The term "gene" encompasses both cDNA and genomic forms of a gene.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

As used herein, the term "expression" refers to the transcription and translation of a gene. Such transcription and translation may be in vivo or in vitro.

As used herein, the term "high level of expression" refers to the expression of a gene, such that the gene product is produced at a 2 to 10-fold greater level of TGF-β or IL-10, by cell populations than is observed following "physiological induction of TGF-β or IL-10," such as that induced by feeding antigen and eliciting oral tolerance. In particularly preferred embodiments, the TGF-β produced at high levels of expression is TGF-β1.

The term "transfection" as used herein refers to the introduction of foreign DNA into eukaryotic cells. Transfection may be accomplished by a variety of means known to the art including but not limited to calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

As used herein, the term "symptoms of IBD" refers to symptoms associated with IBD, including, but not limited to abdominal pain, diarrhea, rectal bleeding, weight loss, fever, loss of appetite, and other more serious complications, such as dehydration, anemia and malnutrition. A number of such symptoms are subject to quantitative analysis (e.g., weight loss, fever, anemia, etc.). Some symptoms are readily determined from a blood test (e.g., anemia) or a test that detects the presence of blood (e.g., rectal bleeding).

The phrase "substantial elimination of said symptoms" refers to a qualitative or quantitative reduction in detectable symptoms (e.g., "symptoms of IBD"), including but not limited to a detectable impact on the rate of recovery from disease (e.g., rate of weight gain).

As used herein, the term "host" refers to anything that can be "transfected" with a "vector." Said host may be a single cell, a tissue, an organ, or an entire organism. For example, a "host" may include, but is not limited to, a cell (e.g., a T-cell), a mouse or a human.

As used herein, the term "delivery system" refers to a method of delivering a "vector" to a host (e.g., "intranasal administration"). As used herein, the term "intranasal administration" refers to a "delivery system" wherein the "vector" is administered by placing it in the intranasal area of the "host" (e.g., by use of a nasal spray or a nebulizer). The vector may be administered alone or in an aqueous suspension containing, but not limited to water, buffer, salts, sodium carboxymethylcellulose, sorbitol and/or dextran. The suspension may also contain stabilizers.

As used herein, the term "homolog" refers to an amino acid sequence that exhibits greater than or equal to 50% homology (identity) with a specific amino acid sequence (e.g., SEQ ID NO:1). In some embodiments, the homology is greater than 60%. In preferred embodiments, the homology is greater than 70%. In still other embodiments, the homology is greater than 80%. For example, the term encompasses (but is not limited to) the TGF-β sequences set forth in Tables 1-4, herein.

As used herein, the term "variant," when referring to a "variant" of TGF-β or "variant" of an TGF-β homolog is defined as a nucleotide sequence that differs in sequence from SEQ ID NO:1 or an TGF-β homolog (e.g., by having deletions, insertions, and substitutions that may be detected using hybridization assays). For example, the term encompasses (but is not limited to) the TGF-β sequences set forth in Tables 1-4, herein.

As used herein, the term "sample" is used in its broadest sense. In one sense it can refer to a tissue sample. In another sense, it is meant to include a specimen or culture obtained from any source, as well as biological. Biological samples may be obtained from animals (including humans) and encompass fluids, solids, tissues, and gases. Biological samples include, but are not limited to blood products, such as plasma, serum and the like. These examples are not to be construed as limiting the sample types applicable to the present invention.

GENERAL DESCRIPTION OF THE INVENTION

The present invention provides compositions comprising nucleic acid constructs encoding TGF-β for the treatment of autoimmune diseases (e.g., inflammatory bowel disease). Furthermore, the invention provides methods for the use of these compositions for the treatment of inflammatory bowel disease. In particularly preferred embodiments, the present invention provides regulated plasmid constructs capable of inducing TGF-β production. In alternative particularly preferred embodiments, the present invention provides regulated plasmid constructs capable of inducing TGF-β1 production.

In preferred embodiments, the present invention provides compositions and methods for the treatment of IBD. Generally, the invention provides vectors and methods for the treatment of IBD. The present invention also provides methods for detecting expression of a gene, such as a reporter gene, from a promoter. The present invention also provides methods for assaying the effect of compounds on cell cytokine production in the presence of TGF-β. In some embodiments, the present invention provides novel inducible vectors providing the cytokine TGF-β for treatment of IBD. The present invention also provides methods for treatment of autoimmune diseases (e.g., IBD) that avoid the detrimental side effects of long term drug therapies such as corticosteroids and immunosuppressants.

Some embodiments of the present invention comprise vectors providing a gene and an inducible promoter. The gene may be a cytokine (e.g., TGF-β or a reporter gene (e.g., β-galactosidase). In some embodiments the vector contains a second gene (e.g., rtTA). In some preferred embodiments, the vector comprises two promoters (e.g., CMV and TRE-CMV). In some particularly preferred embodiments, the two promoters are arranged in opposite orientation.

In some embodiments, the compositions and methods of the present invention are directed towards measuring the expression of a gene (e.g., β-galactosidase) in a host cell (e.g., a T-cell). In some embodiments, a cell expressing a gene (e.g. TGF-β) is treated with compounds and the effects of the compounds on cell cytokine production is measured. In some embodiments, the expression of the gene (e.g., TGF-β) is measured directly in tissues (e.g., colon or spleen) using an immunoassay system (e.g., immunofluorescence). Is some embodiments, expression of mRNA from the gene is measured directly by RT-PCR.

In some embodiments, the compositions and methods of the present invention are directed towards treatment of autoimmune disease (e.g., IBD) using novel expression vectors. In some embodiments, the vector comprises a gene under the control of the inducible TRE-CMV promoter. In some preferred embodiments, the vector of the present invention contains the gene for TGF-β, a cytokine involved in the control of autoimmune responses. The TRE-CMV promoter provides inducible control of the expression of TGF-β, allowing the expression of the gene to be controlled by administration of an antimicrobial. In other embodiments, the methods of the present invention comprise administration of the vector to an individual suffering from an autoimmune disease (e.g., IBD). In some embodiments, administration is through a non-invasive nasal spray. Following administration, expression of TGF-β does not result until the inducer (i.e., an antimicrobial), is administered. Expression can be stopped when the inducer is removed. Induction of TGF-β expression results in the substantial elimination of symptoms of IBD.

The compositions of the present invention provide a vector for tight, inducible regulation of the expression of a gene. In other embodiments, the compositions and methods of the present invention provide an assay for the expression of a gene directly in the tissue where it is being expressed. The compositions and methods of the present invention solve many of the problems of the current treatments for IBD. In addition, the present invention has few of the side effects associated with conventional long term drug therapies. For example, the treatment with TGF-β can be stopped and started at will, preventing potential side effects of the long term use of drug therapies such as corticosteroids. The treatment of the current invention is a DNA vector, which is inexpensive to produce and administer, unlike current therapies. In addition, since treatment is administered in a non-surgical, outpatient manner, the cost and complications of surgery are avoided.

DETAILED DESCRIPTION OF THE INVENTION

The present invention provides compositions comprising nucleic acid constructs encoding TGF-β for the treatment of autoimmune diseases (e.g., inflammatory bowel disease). Furthermore, the invention provides methods for the use of these compositions for the treatment of inflammatory bowel disease. In particularly preferred embodiments, the present invention provides regulated plasmid constructs capable of inducing TGF-β production.

In some embodiments, the present invention comprises vectors providing a gene and a promoter. In some preferred embodiments, the present invention comprises compositions and methods for detecting the expression of a gene in a cell. In some embodiments, the present invention comprises compositions for measuring the effect of a compound on cell cytokine production in the presence of TGF-β. In other embodiments, the invention provides compositions and methods for treatment of autoimmune diseases (e.g., IBD). The compositions of the present invention include vectors comprising the cytokine TGF-β and an inducible promoter. The methods of the present invention comprise transfecting a cell with the vectors. In particularly preferred embodiments, the cell may be part of a host exhibiting symptoms of IBD. In preferred embodiments, administration of the vector results in substantial elimination of the symptoms of IBD.

I. Cytokines and Autoimmune Disease

The present invention compositions and methods for the use of the cytokine TGF-β for the treatment of autoimmune disease, for example, IBD. Cytokines are part of the complex regulatory circuit that controls autoimmune responses. TGF-β influences growth and differentiation of precursors for multiple hematopoietic lineages, the proliferation and migration of mature immune cells into sites of injury or response, and even the suppression of such responses once they have been established (Letterio and Roberts, Clin. Immunol.

Immunopath., 84: 244-250 [1997]). It is the suppression of autoimmune responses that is the most relevant to the present invention. Although an understanding of the mechanisms involved in immune response suppression and activation are not necessary in order to use the present invention, it is believed that TGF-β regulates immune responses by suppressing autoreactive T-cells (Falcone and Sarvetnick, Curr. Opin. Immunol., 11:670-676 [1999]).

TGF-β has been used as therapy for autoimmune diseases. For example, a DNA vector containing TGF-β has been used as treatment for autoimmune diseases. Naked plasmid DNA vectors have the advantage of being maintained episomally for prolonged periods of time without incorporating into the genome. This is favorable, as integration of foreign DNA into the genome can lead to associated mutagenesis (Wolff, et al., Hum. Mol. Genet., 1:363 [1992]). DNA encoding TGF-β administered mucosally to mice has been shown to suppress an immunoinflammatory response to HSV infection (Kuklin et al., J. Clin. Invest., 102:438 [1998]). In addition, TGF-β containing vectors have been used to treat animal models of autoimmune diabetes, EAE, and inflammatory bowel diseases with positive results (See e.g., Prud'homme et al., J. Autoimmunity, 14:23-42 [2000]; and Giladi et al., E. J. Gastroenterol. Hepatol., 7:341 [1995]).

II. Vectors for Gene Expression

In some embodiments, the present invention comprises vectors, wherein the vectors further comprise a gene of interest and a promoter(s). The present invention is not meant to be limited by the choice of promoter or gene. Indeed, genes and promoters other than those described herein are contemplated by the present invention.

A. Genes

In some embodiments, the gene encodes a reporter gene, (e.g., β-galactosidase, GFP, CAT, or luciferase). In some embodiments, the reporter gene is used, for example, to measure, analyze, and/or detect expression patterns of certain vectors in cells, tissues, and hosts. In some embodiments, the reporter gene is used to measure, detect, or analyze the level of control of an inducible promoter (e.g., the lack of expression in the absence of the inducing agent) or to test the level of expression of a given promoter.

In other embodiments, the gene encodes a protein involved in the regulation of autoimmune responses, for example, but not limited to, cytokines (See e.g., Falcone and Sarvetnick, Curr Opinion Immunol., 11:670-676 [1999]). In some preferred embodiments, the gene encodes TGF-β. The present invention is not limited to any one TGF-β gene. Indeed, the present invention contemplates many different TGF-β genes. Some examples of TGF-β genes from a variety of organisms are given in Table 1, along with protein data bank accession numbers. However, in preferred embodiments, the gene encodes a mutant porcine TGF-β1 that does not require activation (SEQ ID NO:1, shown in FIG. 1) (See also, Samuel et al., EMBO J. 11:1599-1605 [1992]). The TGF-β1 of SEQ ID NO:1 is a mutant in which cystines at positions 223 and 225 have been replaced by serines.

Still other embodiments of the present invention provide homologs, mutant, and variant forms of TGF-β. Homologs of TGF-β include but are not limited to an amino acid sequence that exhibits greater than or equal to 50% homology (identity) with a specific amino acid sequence (e.g., SEQ ID NO:1). In some embodiments, the homology is greater than 60%. In some preferred embodiments, the homology is greater than 70%. In still other preferred embodiments, the homology is greater than 80%.

It is possible to modify the structure of a peptide having an activity (e.g., cytokine activity) of TGF-β for such purposes as increased activation (e.g., lack of the need for post-translational activation) or increased cytokine activity (e.g., effect on IBD). Such modified peptides are considered functional equivalents of peptides having an activity of TGF-β as defined herein. A modified peptide can be produced in which the amino acid sequence has been altered, such as by amino acid substitution, deletion, or addition. The assays described below provide method for testing such modified TGF-β nucleic acids and polypeptides.

Moreover, as described above, variant forms (e.g., mutants) of TGF-β are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of TGF-β containing conservative replacements. Conservative replacements are those that take place within a family of amino acids that are related in their side chains. Genetically encoded amino acids are can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (See e.g., Stryer (ed.), *Biochemistry*, pg. 17-21, 2nd ed, WH Freeman and Co. [1981]). Whether a change in the amino acid sequence of a peptide results in a functional variant can be readily determined by assessing the ability of the variant peptide to function in a fashion similar to the TGF-βs described in the experimental section below. Peptides having more than one replacement can readily be tested in the same manner.

TABLE 1

| | TGF-β Genes | |
|---|---|---|
| Gene | Source | Accession Number |
| TGF-β1 | Sheep | I46463; P50414; S45115; CAA54242; AAA51458 |
| TGF-β1 | Rabbit | BAA36950 |
| TGF-β1 | Human | WFHU2; P01137; CAA29283 |
| TGF-β1 | Dog | JC4023; P54831; AAD46993; AAA51458 |
| TGF-β1 | Rat | S10219; P17246; AAD20222 |
| TGF-β1 | Chicken | S01413; P09531 |
| TGF-β1 | Mouse | WFMS2; P04202; NP_035707 |
| TGF-β1 | Deer | AAB05256 |
| TGF-β1 | Carp | AAF22573 |

TABLE 1-continued

TGF-β Genes

| Gene | Source | Accession Number |
|---|---|---|
| TGF-β1 | Pig | P07200; AAA64616 |
| TGF-β1 | Horse | O19011; AAD49431; CAA67801 |
| TGF-β1 | Xenopus | P16176 |
| TGF-β1 | African green monkey | P09533 |
| TGF-β1 | Bovine | P18341; AAA30778 |
| TGF-β1 | Hampster | CAA42838 |
| TGF-β2; short form | Human | A31249 |
| TGF-β2; long form | Human | B31249 |
| TGF-β2 | Human | NP_003229; AAA61162; AAA50405; AAA50404 |
| TGF-β2 | Mouse | WFMSB2; NP_033393; P27090; CAA40672 |
| TGF-β2 | Pig | P09858; AAB03850 |
| TGF-β2 | Rat | Q07257; AAD24484; AAA88514 |
| TGF-β2 | Chicken | P30371; CAA41101; A39489 |
| TGF-β2 | Deer | AAB05257 |
| TGF-β2 | Xenopus | WFXLB2; P17247 |
| TGF-β2; short form | Green Monkey | WFMKB2 |
| TGF-β2 | Bovine | A61439; P21214 |
| TGF-β3 | Mouse | A41397 |
| TGF-β3 | Chicken | A34939; P16047; CAA41128; S36124 |

B. Promoters

The present invention comprises promoters for the expression of genes in cells. In some embodiments, genes are expressed in eukaryotic cells, while in less preferred embodiments genes are expressed in prokaryotic cells. In particularly preferred embodiments, eukaryotic promoters are preferred. However, it is not intended that the present invention be limited to any one promoter. Indeed, multiple promoters are contemplated. For example, promoters for suitable for use in the present invention for expression in eukaryotic cells include, but are not limited to CMV, RSV, SV40, CAG, and SP1. In preferred embodiments, the cytomegalovirus (CMV) promoter is utilized. In some preferred embodiments, the CMV promoter is derived from pCI (Promega Corp., Madison, Wis.). The CMV immediate-early enhancer/promoter region present in the pCI Vector allows for strong, constitutive expression in a variety of cell types. The promiscuous nature of the CMV enhancer/promoter has been demonstrated in transgenic mice, where expression of the chloramphenicol acetyltransferase (CAT) gene regulated by the CMV enhancer/promoter was observed in 24 of the 28 tissues examined (Gluzman, Cell 23: 175 [1981])

Eukaryotic promoter elements may also contain activator, regulatory and enhancer elements. These include, but are not limited to, poly adenylation signals (e.g., SV40 late polyadenylation signal), response elements (e.g., TRE response element), and activators (e.g., rtTA).

Polyadenylation signals terminate transcription by RNA polymerase II and cause the addition of approximately 200 to 250 adenosine residues to the 3'-end of the RNA transcript (Kozak, Proc. Natl. Acad. Sci. USA 83:2850 [1986]). Polyadenylation has been shown to enhance RNA stability and translation (See, Kozak, Mol. Cell. Biol., 9:5134 [1989]; and Rao et al., Mol. Cell. Biol., 8:284 [1988]). To facilitate efficient processing of cloned DNA inserts not containing polyadenylation signals, the SV40 late polyadenylation signal is positioned downstream from the gene of interest. The SV40 late polyadenylation signal is extremely efficient and has been shown to increase the steady-state level of RNA approximately five-fold more than the SV40 early polyadenylation signal (Lusky and Botchan, Nature 293:79 [1981]).

The Tc-controlled transactivator (rtTA) encoded by pTet-Off (Clontech) is a fusion of the wild-type TetR (tetracycline repressor protein) to the VP16 activation domain (AD) of herpes simplex virus. The rtTA, in combination with doxycycline, binds to the TRE element and activates transcription of the adjoining promoter (e.g., CMV). In some embodiments, one or more of these elements may be combined.

In some illustrative examples of the present invention, a vector comprising one promoter is utilized. In these examples, a cytomegalovirus (CMV) promoter is utilized. The CMV promoter controls the expression of the gene of interest (e.g., TGF-β or β-galactosidase). In these examples, the vector also comprises the SV40 late poly (A) gene.

In other embodiments, a vector comprising two promoters is utilized. In these embodiments, it is preferred that one promoter be a CMV promoter that controls the expression of a regulatory transcription factor (rtTA, described above). In such embodiments, it is preferred that the second promoter comprise a TRE-CMV promoter (described above). The TRE-CMV promoter controls the expression of the gene of interest (e.g., TGF-β or β-galactosidase). In this embodiment, the rtTA, in combination with doxycycline, controls the expression of the gene of interest. It is preferred that the two promoter/gene combinations be placed in opposite orientation and that they both be flanked by SV40 late poly (A) genes.

C. Vector Construction

The present invention is not intended to be limited to the methods described for the construction of the vectors described below. As known in the art, various methods are useful for the construction of vectors in addition to those that are described herein. Furthermore, additional vectors find use in the compositions and methods of the present invention.

In some illustrative examples of the present invention, the pCMV-TGF-β vector is employed (a map of pCMV-TGF-β is shown in FIG. 2). pCMV-TGF-β contains a TGF-β gene obtained in cDNA form from pPK9a (Samuel et al., EMBO J., 11:1599-1605 [1992]). The TGF-β was excised from pPK9a by restriction enzyme digest and subcloned into the pSL1180 superlinker vector (Amersham Pharmacia Biotech, Chicago, Ill.). The TGF-β gene was then excised from pSL1180 and inserted into the pCI vector. The pCI vector contains a CMV promoter. The plasmid was amplified in bacteria and purified by $CsCl_2$ centrifugation.

Figure 3:
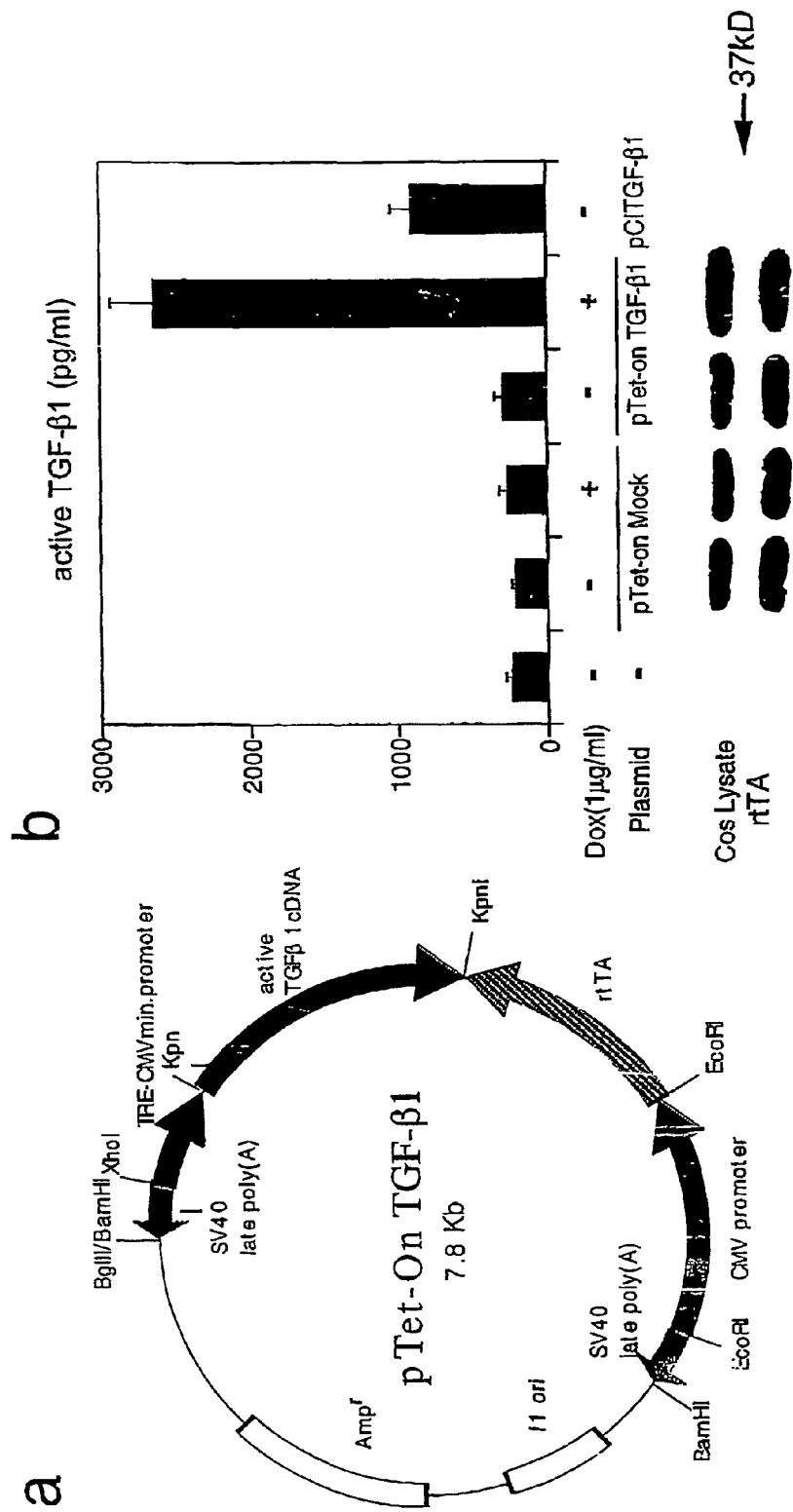

Some embodiments of the present invention comprise the pTet-CMV-TGF-β vector. In other embodiments of the present invention, the pTet-CMV-TGF-β vector is employed for the treatment of autoimmune diseases (e.g., IBD). A map of pTet-CMV-TGF-β (pTet-on-TGF-β1) is shown in FIG. 3. This vector comprises several components, including a TGF-β gene, a TRE-CMV promoter, a CMV promoter, a rtTA gene, and two SV40 late poly (A) genes. In preferred embodiments, pTet-CMV-TGF-β comprises a rtTA gene under the control of a CMV promoter and a TGF-β gene under the control of a TRE-CMV promoter. It is preferred that the two promoter/gene combinations be placed in opposite orientation and that they both be flanked by SV40 late poly (A) genes. The construction of the pTet-CMV-TGF-β vector with the two promoter/gene combinations and the poly (A) has the advantage of tightly controlled expression of the TGF-β. This is an improvement over other non-inducible and inducible vectors with leaky expression.

In some preferred embodiments, pTet-CMV-TGF-β is prepared by the method described below. However, it is not intended that the present invention be limited to this method.

Indeed, other suitable methods of constructing pTet-CMV-TGF-β are contemplated by the present invention. In some preferred embodiments, the TGF-β gene is obtained in cDNA form from pPK9a. In this embodiment, the TGF-β is excised from pPK9a (described above) by restriction enzyme digest and subcloned into the pSL1180 superlinker vector. In some preferred embodiments, the CMV promoter is obtained by restriction digest from pCI. In other preferred embodiments, the TRE-CMV promoter is obtained by restriction digest from pRetroOn and pCI. In still other preferred embodiments, the SV40 late poly A genes are obtained from pCI. It is also preferred that the elements be combined in a pCI vector. In addition, in some preferred embodiments, several steps of sub-cloning are used in the construction of pTet-CMV-TGF-β.

In some embodiments of the present invention, pCMV-β-gal is utilized. pCMV-β-gal is identical to pCMV-TGF-β, with the exception that the TGF-β gene is replaced with the β-galactosidase gene.

A particularly beneficial feature of preferred embodiments of the present invention is the autoregulatory one-gene system in which various gene elements are incorporated into a single construct with the CMV-promoter rtTA-VP16 transcription unit and the TRE-CMV minimum TGF-β1 transcription unit mounted in opposite orientation, in addition to poly A sites that are mounted on either side of these cassettes. Although several Tet regulatable genes suitable for in vivo use have been developed, these are typically two-gene systems that require mating of transgenic mice carrying the separate genes, in order to produce a mouse with the desired double gene pairs. In view of current transfection efficiencies, such gene systems have only limited applications for human therapies, because both genes must be present in the same cell. In addition, the autoregulatory one gene system provided by the present invention is not leaky (i.e., it does not produce TGF-β1 in the absence of doxycycline). Although an understanding of the mechanism(s) is not necessary in order to use the present invention and it is not intended that the present invention be limited to any particular mechanism(s), it is believed that the transfection of TGF-β1 mRNA not induced by rtTA interaction with TRE is blocked (i.e., subtracted) by constitutive transcription of rtTA-VP16 mRNA proceeding in the opposite direction. This feature of the preferred plasmids of the present invention does not lead to TGF-β1 synthesis and secretion in the absence of doxycycline. Thus, recipients of the plasmid are not exposed to plasmid-derived TGF-β1 in the absence of doxycycline. A second feature of the pTet-on-TGF-β1 plasmid is that the amount of TGF-β1 produced by transfected cells is 2 to 5-fold higher than the non-regulatable plasmid pCI-TGF-β1. While in both cases the TGF-β1 gene is under the control of a CMV promoter, it is probable that the CMV promotor fused to an activated TRE is a more active promoter than the CMV promoter alone. Furthermore, it is possible that the TRE-activated CMV promoter may be less dependent upon the presence of an inflammatory milieu than the pCI-TGF-β1 plasmid for high level TGF-β1 induction. This is a distinct advantage in situations in which TGF-β1 secretion is desired prior to the onset of inflammation. In addition, the preferred plasmid construct of the present invention finds use in the delivery of other suppressor cytokines in addition to TGF-β1, such as IL-10. Indeed, as pTet-on-TGF-β1 expression also leads to massive IL-10 responses, it is in effect, delivering both TGF-β1 and IL-10 to the host system.

The present invention provides additional advantages over prior art plasmids. For example O'Brien et al. (O'Brien et al., Gene 184:115-120 [1997]) describe a one-gene plasmid which contains both Tet-off and raf genes positioned in the same direction and separated by a transcriptional terminator. However, while pTet-on-TGF-β1 is approximately 5.9 kb without TGF-β1 cDNA, the size of the one-gene plasmid described by O'Brien et al. without raf cDNA is 10 kb. Thus, the in vivo transfection efficiency of the O'Brien et al. plasmid is questionable.

Gould et al. (Gould et al., Gene Ther., 7:2061-2070 [2000]) describe a self-contained Tet-on plasmid in which the promoter elements were also in the opposite direction. However, in this case, the poly A sites are located in the middle of two gene elements. In addition, while pTet-on-TGF-β1 produced 3-fold more TGF-β1 than the non-regulatable pCI-TGF-β1 in vitro, the Gould et al. Tet-on plasmid expressed lower luciferase activity than a control non-regulatable plasmid with a CMV promoter. Furthermore, while several retroviral one-gene Tet-off systems have been reported, an efficient Tet-on retroviral system which is active in vivo has not been described. In addition, plasmids based on Tet-off systems are not as useful as those based on Tet-on systems, because in the former case, the patient must always be given an antimicrobial to provide rtTA expression.

Studies of the on-off features of the regulatable plasmid of the present invention indicated that transcription is in fact highly responsive to the presence of doxycycline. Thus, while the administration of a non-regulatable plasmid was marked by the cessation of RNA transcription about two weeks after plasmid administration and loss of DNA after about four weeks, the cessation of RNA transcription occurs within days after cessation of doxycycline administration and the total period of exposure to TGF-β1 during experimental colitis is shortened from 12 days to 4 days. Since the regulatable plasmid in preferred embodiments of the present invention leads to a shortened exposure time without compromising control of inflammation, it has a clear therapeutic advantage over non-regulatable plasmids.

III. Expression of Genes from Vectors

The vectors described above can be expressed in cells. In one embodiment of the invention, the vectors are transfected into cells and the expression of the gene contained in the vector detected (e.g., measured). The invention is not intended to be limited by the gene nor cell chosen for expression. In some embodiments, the cell to be transformed is part of a host. In some embodiments of the present invention, the vector may contain a reporter gene, including but not limited to β-galactosidase, GFP, luciferase, and CAT, to measure gene expression. In other embodiments, the gene is TGF-β.

In some embodiments, the cell transfected is a tissue culture cell transfected with a vector containing a reporter gene, such as pCMV-β-Gal. Expression of a reporter gene may be detected using any suitable method. For example, expression of β-galactosidase may be detected using a substrate for β-galactosidase (e.g., ONPG, (o-nitrophenyl-b-D-galactopyranoside)) and measuring the change in optical density resulting from β-galactosidase activity spectrophotometrically.

In some embodiments, the cell transfected is part of an animal (e.g. a mouse or a human). In some embodiments, when the vector is administered to an animal, it may be administered pulmonarily, (e.g., by inhalation or insufflation of powders or aerosols, including by nebulizer; intratracheal, intranasal, epidermal and transdermal). In other embodiments, the vector may be administered topically, orally or parenterally. In some preferred embodiments, the vector is administered intranasally. Parenteral administration includes intravenous, intraarterial, subcutaneous, intraperitoneal and intramuscular injection or infusion; as well as intracranial, intrathecal or intraventricular administration. In some embodiments, cells in several tissues will contain the vector and express the gene of interest.

Administration of the preferred plasmid of the present invention has been shown to deliver the plasmid into macrophages and T-cells present in inflammatory sites. In addition, unlike high and repeated doses of recombinant adenoviral vectors which generate neutralizing antibodies and inflammatory responses, intranasal delivery of the plasmid of preferred embodiments of the present invention can be re-administered several times without apparent loss of efficacy.

Expression of the gene (e.g., β-galactosidase) may be detected by any suitable method. It is not intended that the method of detection be limited to those described herein but can encompass other methods known in the art. One method that may be used is confocal immunofluorescence. When using confocal immunofluorescence, the expression of protein from the gene of interest is detected in whole cells isolated from tissue samples. Tissues samples that may be assayed include, but are not limited to spleen and colon cells. Cells that may be assayed include, but are not limited to T-cells. In some embodiments, CD4+ and/or CD3+ T-cells are assayed, while in other embodiments, CD11b+ macrophages are also assayed. The protein expressed is labelled with an antibody specific to the protein. An additional antibody may be used that is specific for a cell type, including but not limited to, those described above. In these embodiments, each of the two antibodies is labelled with a different fluorescent cytochrome. The two fluorochromes are chosen such that they fluoresce at different wavelengths. Fluorochromes that may be employed include, but are not limited to Texas-Red and FITC.

Another embodiment of the present invention involves detecting genes encoded by the vectors of the present invention. In some embodiments, the methods comprise detection of expression of mRNA from the gene of interest. The technique of PCR may be utilized in this embodiment. In some embodiments, PCR is used to detect DNA, while in other embodiments, PCR is used to detect RNA. In either of these embodiments, the DNA or RNA is typically first isolated from tissues. The present invention is not limited by the method of isolation. For example, DNA may be isolated by commercially available kits. RNA may be isolated by known methods, such as extraction with guanidinium isothiocyanate. When DNA is the substrate for PCR, standard PCR methods known to those in the art are employed. When RNA is the substrate, Reverse Transcriptase PCR (RT-PCR), as known in the art is utilized. Techniques and protocols for PCR and RT-PCR are well-known and readily available in the art (See e.g., Ausbel et al., eds. *Current Protocols in Molecular Biology*, New York, John Wiley & Sons, Inc. [1994]). Alternatively, RNA or DNA may be detected by a hybridization assay, including but not limited to, Southern or Northern analysis (See e.g., Ausbel et al., supra). These methods involve hybridization of a nucleic acid probe specific for the RNA or DNA of interest. The probe is labelled (e.g., radioactively) and detected using any suitable method (e.g., autoradiography or phosphorimaging).

IV. Use of TGF-β to Treat TNBS Colitis

The vectors described above may also be used in the treatment of IBD. The expression of TGF-β from the vectors described above was effective in preventing symptoms of intestinal inflammation in a mouse model of IBD. Illustrative examples are given in Examples 3 and 7. These examples utilize a mouse model of IBD that mimics the chronic intestinal inflammation of IBD. The mouse model involves the intra-rectal administration of trinitrobenzene sulfonic acid (TNBS), a haptenizing reagent. A dose of from 0.5-2.5 mg is generally administered. Administration of TNBS results in acute colitis, as evidenced by weight loss, histological changes in colon tissue, and decreased survival (See e.g., Neurath et al., J. Exp. Med., 183:2605 [1996]).

In one illustrative Example (described in Example 3B), mice are treated with 2.5 mg TNBS to induce colitis. In this example, administration is given intra-rectally. At the same time, some of the mice are treated with pCMV-TGF-β. In this example, mice are given 100 μg of plasmid DNA intranasally. Two control groups are utilized. The first control group was not given TNBS, while the second was given TNBS but not plasmid DNA. The success of the treatment was assayed by monitoring the weight and survival rate of the mice following treatment. Results (shown in FIGS. 5 and 6) demonstrated that treatment with pCMV-TGF-β prevented weight loss and increased the survival rate relative to the controls described above. Symptoms of colitis in the mice of Example 3B were also assayed by histological assessment of tissue samples (described in Example 4). Mice treated with pCMV-TGF-β exhibited low levels of inflammation similar to control groups while untreated mice exhibited high levels of inflammation (Table 2). These results demonstrated that intranasal expression of a plasmid expressing TGF-β can prevent mice symptoms of colitis in mice administered TNBS.

Figure 6:
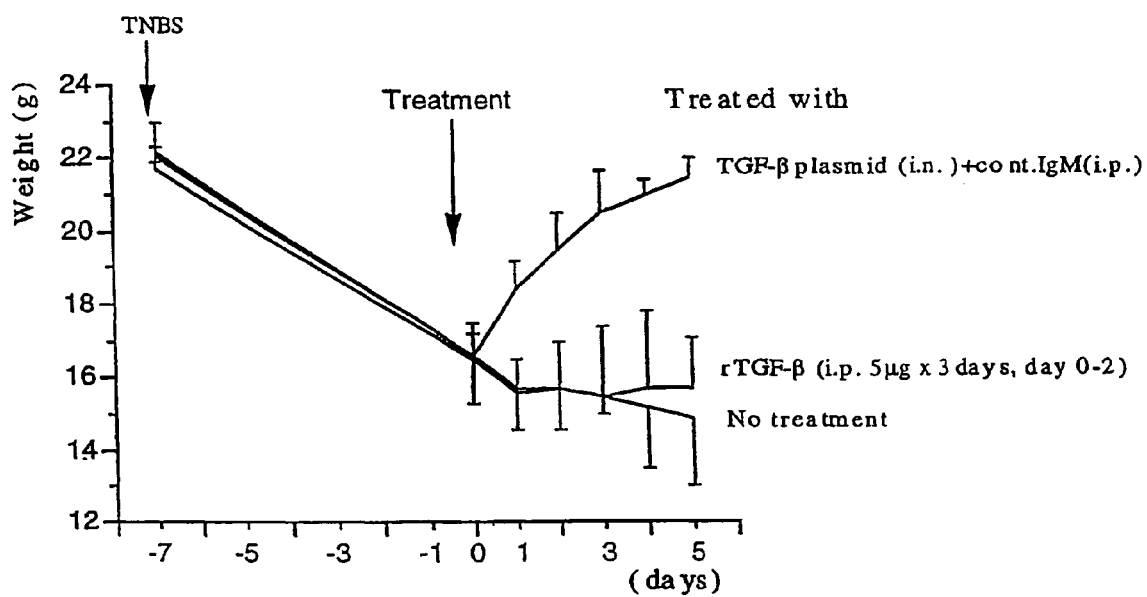
FIG. 6 shows the weight of mice with TNBS colitis following treatment with intranasal pCMV-TGF-β1 and rTGF-β1 in one embodiment of the present invention.

In another illustrative example (Example 3C), mice exhibiting active colitis were treated with either pCMV-TGF-β or rTGF-β1 protein. Mice given pCMV-TGF-β regained lost weight within 5 days of administration, while untreated mice continued to lose weight (FIG. 6). Mice given rTGF-β1 protein did not regain lost weight, but instead stabilized their weight at disease-state levels. Symptoms of colitis in the mice of Example 3C were also assayed by histological assessment of tissue samples (described in Example 4). Mice treated with pCMV-TGF-β exhibited low and intermediate levels of inflammation. However, mice treated with rTGF-β1 protein and those not treated exhibited high levels of inflammation (Table 3). These results demonstrated that in addition to preventing the onset of symptoms, pCMV-TGF-β (and not rTGF-β1) can treat existing colitis.

Figure 7:
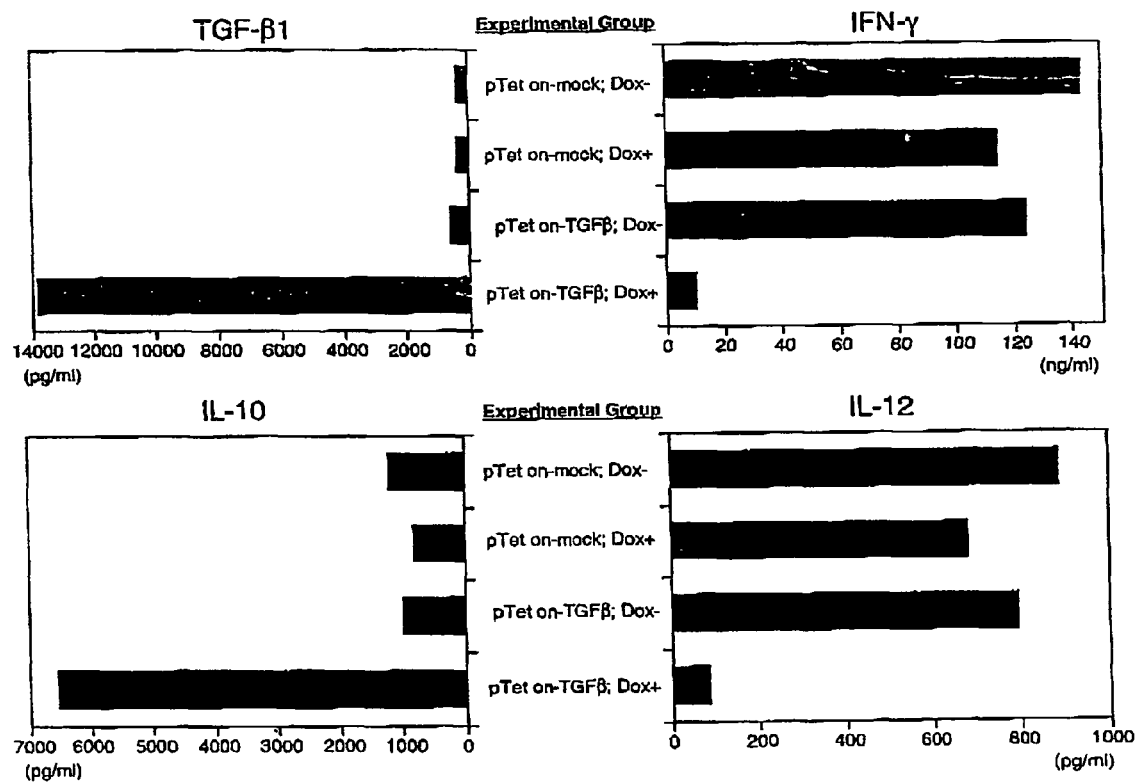
FIG. 7 shows levels of cytokine secretion by colonic lamina propria T-cells of the mice in one embodiment of the present invention.

In another illustrative example of the present invention (Example 7), mice were administered pTet-CMV-TGF-β. In Example, mice were given 100 μg of plasmid DNA intranasally. Four days later, half of the mice were administered the antibiotic doxycycline to induce expression of TGF-β. In this experiment, mice were given 500 μg doxycycline I.P. Three days later, mice were treated with 2.5 mg TNBS to induce colitis. In this example, administration was given intra-rectally. Mice given both the vector and doxycycline exhibited decreased weight loss relative to mice not given doxycycline (FIG. 7). Symptoms of colitis in the mice of Example 7 were also assayed by histological assessment of tissue samples (described in Example 4). As shown in Table 4, the mice treated with pTet-CMV-TGF-β and doxycycline exhibited low levels of inflammation while those treated with only pTet-CMV-TGF-β exhibited high levels of inflammation. This result illustrated that the expression of TGF-β can be controlled using pTet-CMV-TGF-β and doxycycline. This result also illustrated that inducing TGF-β expression before inducing colitis can prevent the onset of symptoms of colitis.

V. Cytokine Production

In one embodiment of the present invention, the doxycycline-regulated plasmid provides means to induce high levels of cytokines. In particular, the present invention provides means for the induction of a high level of IL-10 following expression of pTet-on-TGF-β1.

In vivo administration of naked plasmid DNA, such as that provided by the present invention provides beneficial results in autoimmune inflammation therapy as it is capable of inducing cytokine production at specific tissue sites. The use of such therapy to establish cells capable of synthesizing regulatory cytokines, such as IL-10 and/or TGF-β1 is particularly relevant in this context, because cells producing these cytokines, though few in number, have been shown to play a central role in the counter-regulation of several types of experimental models of inflammation. For example, it has been shown that feeding antigens relating to inflammation (i.e., feeding MBP (myelin basic protein) to mice prior to induction of EAE (experimental autoimmune encephalitis), or feeding TNP-haptenated colonic protein to mice prior to induction of TNBS-colitis) leads to the induction of TGF-β-producing mucosal regulatory cells with the potential to prevent EAE or TNBS-colitis respectively. Thus, by inducing regulatory cells via this route of therapy utilizes and perhaps improves a "natural" mechanism of controlling inflammation.

As discussed in greater detail herein, a useful experimental model of mucosal inflammation is the Th1 T-cell inflammation system (i.e., TNBS-colitis) that somewhat resembles Crohn's disease. During the development of the present invention, it was determined that single intranasal doses of a plasmid encoding the active form of TGF-β can not only prevent the onset of TNBS-colitis, but also abrogate established colitis. In contrast, administration of recombinant TGF-β protein was without a therapeutic effect, presumably due to the latter's short half-life. Although an understanding of the mechanism(s) is not necessary in order to use the present invention and it is not intended that the present invention be limited to any particular mechanism(s), administration of the TGF-β1 plasmid leads to high level TGF-β1 production, which in turn induces high level IL-10 production. This production results in suppression of the Th1 inflammation through the suppression of IL-12 and TNF-α production by IL-10, and the down-regulation of IL-12Rβ2 chains, thereby interrupting IL-12 signaling.

VI. Detection of Cytokine Expression

In one embodiment of the present invention, the effect of administering a vector expressing TGF-β (e.g., pCMV-TGF-β or pTet-CMV-TGF-β) to a host on the secretion of cytokines by the host's T-cells is measured. The present invention is not limited to measuring the level of expression of any one cytokine. For example, cytokines that may be measured include, but are not limited to TGF-β and IFN-γ.

A. Ex vivo Detection

In some embodiments, cytokine expression in colonic lamina propria T-cells is measured, while in other embodiments, cytokine expression in splenic T-cells is measured. T-cells are isolated from colon and spleen tissues using any suitable method known in the art (See e.g., Boirivant et al., J. Exp. Med., 188:1929 [1998]). Illustrative examples of the isolation of T-cells from mice treated with TGF-β vectors are given in Examples 6 and 8. Cells are released from the tissues using any suitable method, including but not limited to, digestion with collagenase or by applied pressure. T-cells can be isolated from the cell population by centrifugation in a Percoll gradient and further purified using mouse CD4+ T-cell purification columns (commercially available from R&D, Minneapolis, Minn.). In some embodiments, the cells are cultured following isolation. In some further embodiments, the cells are stimulated with anti-CD3ε or IFN-γ.

Cytokine expression may be measured by ELISA assay. However, the present invention is not limited to detection by ELISA. Protocols for ELISA assays are available in the art (See e.g., Boirivant et al., J. Exp. Med., 188:1929 [1998]). For example, kits for ELISA assays are available for IFN-γ (Endogen) and TGF-β (Promega). Example 6 (results are shown in FIG. 6) illustrates that stimulated colonic T-cells of untreated mice undergoing active colitis secrete high amounts of IFN-γ and low amounts of TGF-β. In contrast, mice treated with pCMV-TGF-β secrete low amounts of IFN-γ and high amounts of TGF-β. Example 8 (results are shown in FIG. 7) illustrates that both stimulated and unstimulated spleen T-cells of mice administered pTet-CMV-TGF-β secrete high amounts of TGF-β when doxycycline was administered and negligible amounts when no doxycycline was administered.

B. In vitro Detection

In some embodiments, the vectors of the current invention are used for the screening of the effect of test compounds on cytokine (e.g., TGF-β) expression of transfected cells. In some preferred embodiments, cells in culture are transfected with a vector, such as pCMV-TGF-β or pTet-CMV-TGF-β. If pTet-CMV-TGF-β is used, doxycycline is added to induce expression of TGF-β. The effect of the expression on cytokine expression can then be detected using the methods described above (e.g., ELISA assay). It is not intended that the present invention be limited to the nature of the compounds used for screening. Indeed, it is contemplated that various compounds will be tested using the present invention. Furthermore, compounds for use in the screening assays of the invention can be obtained from any source. For example, libraries of synthetic and/or natural compounds are particularly useful. Numerous means are currently used for random and directed synthesis of saccharide, peptide, nucleic acid, and small molecule compounds. Synthetic compound libraries are commercially available from Maybridge Chemical Co. (Trevillet, Cornwall, UK), Comgenex Princeton, N.J.), Brandon Associates (Merrimack, N.H.), and Microsource (New Milford, Conn.). In addition, a rare chemical library is available from Aldrich (Milwaukee, Wis.). Libraries of natural compounds in the form of bacterial, fungal, plant and animal extracts are available from Pan Laboratories (Bothell, Wash.) and MycoSearch (NC). Thus, it is contemplated that the present invention will find use in testing a wide variety of compounds.

VII. Therapy for Autoimmune Disease

In particularly preferred embodiments, the present invention provides compositions and methods for the treatment of autoimmune disease. Although experiments conducted during the development of the present invention demonstrate that the present invention is beneficial in the treatment of autoimmune diseases (e.g., Th1-mediated chronic diseases such as Crohn's disease), it is recognized that excessive exposure to TGF-β can consequently lead to tissue fibrosis. Thus, experiments were conducted as described herein, in order to assess the potential for the development of fibrosis related to the administration of the plasmids encoding TGF-β1 of the present invention.

In early experiments using a mouse model, no lung fibrosis was observed, even though the route of administration of the TGF-β1 plasmid to the mice was intranasal. Nonetheless, it was clear that tight regulation of plasmid TGF-β1 production is necessary, so that the length of exposure to TGF-β1 is as brief and focused as possible. Thus, a plasmid encoding TGF-β1 that is regulated by doxycycline, such that TGF-β1 is produced only when the plasmid is co-administered with doxycycline was produced. The experiments described herein show that this regulatable plasmid is a highly effective means of preventing and/or treating TNBS-colitis, even though the exposure time to TGF-β can be relatively short (i.e., approximately 4 days). In addition, the results discussed herein indicate that instead of acting as a cause of fibrosis, the regulatable plasmid prevents fibrosis (e.g., fibrosis caused by a well-known fibrosis-inducing agent, bleomycin). Indeed, mice treated with intranasal pTet-on-TGF-β1 plus doxycycline did not exhibit fibrotic changes in their colons or other tissues (e.g., lung, liver, spleen, and kidney) as observed using hematoxylin and eosin staining at 5, 14, 28, and 56 days following plasmid and TNBS administration.

Although an understanding of the mechanism(s) is not necessary in order to use the present invention and it is not intended that the present invention be limited to any particular mechanism(s) recent work concerning the mechanism of counter-regulation of autoimmune inflammation in general and in mucosal inflammation in particular, suggests that such regulation is mediated either by "Th3" T-cells producing TGF-β1 or by TR1 T-cells producing mostly IL-10. Experiments conducted during the development of the present invention using the TNBS-colitis model to analyze counter-regulation strongly suggest that TGF-β is the primary suppressor cytokine, at least with respect to Th1-mediated mucosal inflammation, but requires IL-10 to ameliorate the IL-12/IFN-γ response, which would otherwise prevent the expansion of TGF-β1-producing T-cells. This is in agreement with other data obtained during the development of the present invention, which indicated that cells producing TGF-β induced by plasmid administration could suppress TNBS-colitis, even in the absence of IL-10, since in this situation, TGF-β1-producing cells can be induced by plasmid administration in the face of a Th1 response. In addition, while previous studies suggest that IL-10 may be necessary for down-regulation of IL-12 production, TGF-β1 can operate in its absence, since TGF-β1 interferes with IL-12 signaling via down-regulation of IL-12R β2 chains.

This latter effect of TGF-β1 bears on an important aspect of the present invention, in that high levels of TGF-β1 secretion need to be present only for a short period of time, in order to ameliorate TNBS-colitis. Although an understanding of the mechanism(s) is not necessary in order to use the present invention and it is not intended that the present invention be limited to any particular mechanism(s), it is likely that this relates to the fact that TGF-β1 mediates down-regulation of the IL-12R β2 chain as indicated above. This, in turn, deprives Th1 T-cells of an essential growth factor and leads to apoptosis of the latter cells and resolution of the colitis.

VIII. Therapy for IBD

In one embodiment of the present invention, vectors expressing TGF-β are used to treat IBD in subjects (e.g., humans). In preferred embodiments, the vector is pTet-CMV-TGF-β. However, the present invention is not intended to be limited to the vectors disclosed above. In some embodiments the vectors contain the TGF-β of SEQ ID NO:1, while in other embodiments, the vectors contain wild type human latent TGF-β1, human latent TGF-β3, or mouse latent TGF-β1. In other embodiments, variants or homologs (described above) of SEQ ID NO:1 are utilized.

In some particularly preferred embodiments of the present invention, the vectors are administered to humans having symptoms of an autoimmune disease (e.g., IBD). As discussed above, symptoms of IBD include, but are not limited to, abdominal pain, diarrhea, rectal bleeding, weight loss, fever, loss of appetite, and other more serious complications, such as dehydration, anemia and malnutrition. A number of such symptoms are subject to quantitative analysis (e.g., weight loss, fever, anemia, etc.). Some symptoms are readily determined from a blood test (e.g. anemia) or a test that detects the presence of blood (e.g., rectal bleeding).

Although the present invention is not so limited, in some preferred embodiments, the vector is administered intranasally. Thus, in other embodiments, administration is topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial (e.g., intrathecal or intraventricular), administration.

Compositions and formulations for intranasal administration include suspensions or solutions in water or non-aqueous media. Solutions for intranasal administration may also contain buffers, diluents and other suitable additives and other pharmaceutically acceptable carriers or excipients. Aqueous suspensions may further contain substances that increase the viscosity of the suspension including, for example, sodium carboxymethylcellulose, sorbitol and/or dextran. The suspension may also contain stabilizers. Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be administered in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents (e.g., lubricants, preservatives, stabilizers, wetting agents, emulsifiers, salts for influencing osmotic pressure, buffers, colorings, flavorings and/or aromatic substances and the like) which do not deleteriously interact with the nucleic acid(s) of the formulation.

Clinical dosages may be within a large range where clinical effect is observed (e.g., substantial elimination of the symptoms of IBD). Dosage ranges contemplated include, but are not limited to, 2-20 mg plasmid DNA. Other ranges are contemplated, depending on the weight of the individual and their response to initial dosages. For example, children may be given dosages in a smaller range, including but not limited to, 0.1-5 mg plasmid DNA. In other embodiments, individuals who do not respond to an initial range of dosages may be given higher dosages, including, but not limited to 10-100 mg plasmid DNA.

When pTet-CMV-TGF-β is utilized, doxycycline is also administered to the subject to induce expression of TGF-β.

Due to the inducibility of the pTet-CMV-TGF-β, expression of the vector can be "turned on and off" by administering doxycycline when expression is desired. A dose of 100-200 mg/day doxycycline is contemplated. However, additional dosage ranges are contemplated. If this dosage is not effective, additional ranges may be utilized, including, but not limited to 150-300 mg/day.

In some presently described methods of the invention, a preferred outcome is that administration of the vector results in substantial elimination of the symptoms of IBD. In some embodiments, the vector is administered a single time, while in others, the vector is administered multiple times. In still other embodiments, the vector is administered when relapse of IBD symptoms occur.

The methods and compositions of the present invention are not limited to the treatment of IBD. Indeed, it is contemplated that the methods and compositions of the present invention will find use in the treatment of various other diseases. In particular, it is contemplated that the present invention will find use in the treatment of various diseases with an autoimmune component. Diseases contemplated include, but are not limited to, multiple sclerosis, rheumatoid arthritis, systemic lupus erythematosus, insulin-dependent diabetes mellitus, sarcoidosis, and psoriasis.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: M (molar); mM (millimolar); μM (micromolar); g (grams); mg (milligrams); μg (micrograms); ng (nanograms); ml (milliliters); μl (microliters); cm (centimeters); mm (millimeters); nm (nanometers); U (units); mRNA (messenger RNA); cDNA (copy or complimentary DNA); RPM (revolutions per minute); PCR (polymerase chain reaction); RT-PCR (reverse-transcriptase PCR); ° C. (degrees Centigrade); TNBS (trinitrobenzene sulfonic acid); TGF-β (transforming growth factor beta); IFN-γ (interferon gamma); IL (interleukin, e.g. IL-10, IL-12, etc.); PBS (phosphate buffered saline); HEPES (N-[2-hydroxyethyl]piperazine-N-[2-ethanesulfonic acid]); mAb (monoclonal antibody); Amersham Pharmacia Biotech (Amersham Pharmacia Biotech, Piscataway, N.J.); Amersham Pharmacia (Amersham Pharmacia, Chicago, Ill.); Life Technologies (Life Technologies, Rockville, Md.); Schering-Plough (Schering-Plough Animal Health, Union, N.J.); Sigma-Aldrich (Sigma-Aldrich, St. Louis, Mo.); R&D (R&D, Minneapolis, Minn.); Gentra Systems (Gentra Systems, Minneapolis, Minn.); Promega (Promega Corp., Madison, Wis.); Boehringer Mannheim (Boehringer Mannheim Biochemicals, Indianapolis, Ind.); Becton Dickinson (Becton Dickinson, Sunnyvale, Calif.); Pharmingen (Pharmingen, San Diego, Calif.); Clontech (Clontech, Palo Alto, Calif.); Calbiochem (Calbiochem Co, La Jolla, Calif.); Roche (Roche Molecular Biochemicals, Indianapolis, Ind.); Endogen (Endogen, Woburn, Mass.); Dynatech (Dynatech Labs, Chantilly, Va.); Biofluids (Biofluids Inc., Rockville, Md.); Jackson Immuno (Jackson Immuno Research Laboratories, West Grove, Pa.); Fort Dodge (Fort Dodge Animal Health, Fort Dodge, Iowa); Butler (Butler Company, Columbus, Ohio); Biocolor (Biocolor, Northern Ireland); and Leica Microsystems (Leica Microsystems, Exton, Pa.).

In the following Examples describing experiments conducted using mice, the mice were either specific pathogen-free (SPF) 5-6 week old male SJL/J mice obtained from the National Cancer Institute Animal Facility (Frederick, Md.), or SPF C57BL/6 mice obtained from the National Cancer Institute Animal Facility. Animal use in all of these experiments adhered to NIH Laboratory Animal Care Guidelines.

In experiments involving intranasal administration of plasmid DNA, 20 μL of PBS containing 100 μg of plasmid DNA were administered to mice lightly anesthetized with metophane (methoxyflurance, Schering-Plough). The quality of plasmid DNA administered was verified by electrophoresis on 1% agarose gels, just prior to administration to the animals.

EXAMPLE 1

Production of pCMV-TGF-β Plasmid

In this Example, the production of pCMV-TGF-β plasmid material is described. pCMV-TGF-β is shown in FIG. 2. The construct comprises a TGF-β gene under the control of a CMV promoter. The TGF-β gene used in this vector is of porcine origin. In addition, the TGF-β is a mutant form in which cystines at positions 223 and 225 have been replaced by serines (Dr. P. Kondaiah, Indian Institute of Science, India; Samuel, et al., EMBO J., 11:1599 [1992]). This TGF-β1 is active, but has been designed to preclude binding of nascent TGF-β1 to latency-associated protein (LAP) in the cells.

The plasmid was constructed as described herein. The TGF-β gene, in cDNA form (SEQ ID NO:1) was excised from the plasmid pPK9a (Samuel, et al., EMBO J., 11:1599 [1992]) by digestion with BglII. The cDNA obtained was then subcloned into the BamHI site of the pSL1180 superlinker vector (Amersham Pharmacia Biotech, Chicago, Ill.). The gene was then excised from pSL1180 by digestion with EcoRI and EcoRV and ligated into the EcoRI and SmaI sites of the pCI vector (Promega). The vector obtained was designated pCMV-TGF-β. The plasmid was amplified in E. coli and a large quantity of purified plasmid was prepared by two cycles of CsCl$_2$ ultracentrifugation followed by extensive dialysis against TE buffer and two cycles of ethanol precipitation. The purified plasmid was stored at −70° C. until use.

EXAMPLE 2

Production of pTetCMV-TGF-β1 Plasmid

In this Example, the production of pTetCMV-TGF-β1 is described. This plasmid is shown in FIG. 3. The construct comprises a TGF-β1 gene under the control of a TRE-CMV promoter. The TGF-β1 gene used in this construct is of porcine origin. In addition, the TGF-β1 is a mutant form in which cystines at positions 223 and 225 have been replaced by serines. The plasmid contains a regulatory transcription factor (rtTA) under the control of a CMV promoter. The TGF-β1 is under the control of a TRE-CMV promoter. In the presence of doxycycline and rtTA, the TRE-CMV promoter is activated and TGF-β is produced. The two promoters are placed in opposite directions. Additionally, a polyA gene is located at both ends of the TGF-β cassette to control expression of rtTA. Thus, the plasmid produces TGF-β only in the presence of doxycycline.

The plasmid was constructed as described. The BglII-NotI fragment of pCI (Promega) containing the CMV promoter was excised and inserted into the NotI-BamHI site of pBluescript SK (Stratagene). The CMV promoter was then excised by EcoRI digestion and inserted into the EcoRI site of pRetro-On vector (Clontech) after the removal of the SV40 promotor contained in the pRetro-On vector. The product was termed Retro-on CMV. Then, the BglII fragment of TGF-β cDNA from pPK9a was inserted into BglII site of pSuperlinker 1180 (Amersham Pharmacia). The NotI-BamHI fragment of TGF-β1 cDNA was then inserted into Retro-on CMV. The BglII-XhoI fragment of SV40 late poly (A) was then prepared from pCI and inserted into the BglII-XhoI site of a new pCI vector lacking a CMV promotor. The XhoI-XhoI fragment from pRetro-on CMV (5' region of XhoI site was produced in the first step of this procedure, and the other XhoI end comprising 5' TRE (tet responsive element)) was inserted into XhoI site of pCI plus SV40 poly (A) prepared above. Thus, the CMV promotor-rtTA-TGF-β1-miniCMV-TRE fragment was flanked by both SVpoly(A) ends in the pCI plasmid. This construct is termed "pTet-CMV-TGF-β1," or "pTet-on-TGB-β1."

As shown in FIG. 3, Panel A, this plasmid contains a "reverse" Tet transactivator (rtTA-VP16) under a CMV promoter fused in opposite orientation to the active TGF-β1 construct under a CMV minimum promoter and a tetracycline-responsive element (TRE). The CMV promoter driving rtTA-VP16 is constitutively active, but is enhanced in cells present in an inflammatory milieu. Doxycycline binding to rtTA-VP16 protein enables it to interact with a TRE which in turn activates the CMV minimum-promoter and TGF-β1 transcription. Thus, in the absence of doxycycline, rtTA does not bind to the TRE and there is no TGF-β1 transcription.

The plasmid was amplified in *E. coli* and a large quantity of purified plasmid was prepared by two cycles of $CsCl_2$ ultracentrifugation followed by extensive dialysis against TE buffer and two cycles of ethanol precipitation. The purified plasmid was stored at −70° C. until use.

To verify the regulatability of the pTet-on-TGF-β1 plasmid, both pTet-on-TGF-β1 and mock pTet-on (i.e., pTet not containing a TGF-β1 cDNA construct) were transfected into COS7 cells and the amount of TGF-β1 secreted into the supernatant by the cells in culture in the presence and absence of doxycycline determined. As shown in the Western blot analysis shown in FIG. 3, Panel B), COS7 cells transfected with pTet-on-TGF-β1 or mock pTet-on both produced rtTA-VP16 (37 kD doublets) in the presence and absence of doxycycline. In this Figure, the production of active TGF-β1 in the supernatant of pTet-on-TGF-β1 or pTet-on mock plasmid after three days of transfection into COS cells with and without doxycycline is shown as the mean±SD. The doublet is usually observed during detection of rtTA (37 kD). Nevertheless, abundant TGF-β1 protein was detected only in the supernatants of cells transfected with pTet-on-TGF-β1 cultured in the presence of doxycycline. Thus, while pTet-on-TGF-β1 transfected cells in the absence of doxycycline, and mock pTet-on in the presence or absence of doxycycline, secreted 200-240 pg/ml of active TGF-β1, as measured by ELISA. Cells transfected in the presence of doxycycline with p-Tet-on-TGF-PI produced about 2600 pg/ml TGF-β1 (i.e., a tenfold greater amount). Furthermore, in the presence of doxycycline, pTet-on-TGF-β1 transfected cells produced 3-fold higher amounts of TGF-β1 than pCI-TGF-β1-transfected cells. In addition, pTet-on-TGF-β1 showed virtually no leaky production without doxycycline. The Western blots confirmed that the transfection of each plasmid was successful.

EXAMPLE 3 pCMV-TGF-β Substantially Eliminates Symptoms of TNBS Colitis in Mice

This Example illustrates the use of pCMV-TGF-β to treat mice with TNBS-colitis. In recent studies it has been shown that immune responses against self (autoimmunity) is normally under the control of counter-regulatory or suppressive immune responses that maintain immune homeostasis and prevent disease. This mechanism is very clearly evident in an experimental model of colitis known as TNBS-colitis in which certain strains of mice are rectally administered trinitrobenzene sulfonic acid (TNBS) and thereby develop a severe and chronic colitis mediated by a Th1 T-cell response and the production of IFN-γ.

A. Mouse Model for Colitis

Specific pathogen free, 5-6 wk old male SJL/J mice were obtained from the National Cancer Institute (Frederick, Md.) and maintained in the National Institute of Allergy and Infectious Diseases animal holding facilities (Bethesda, Md.). Mice were treated with a single intra-rectal dose of TNBS (2.5 mg) dissolved in ethanol, a dose that regularly induces severe colitis (Neurath et al., J. Exp. Med., 182:1281 [1995]). Mice were first anesthetized with metophane (methoxylflurance, Schering-Plough). A 3.5F catheter was then carefully inserted into the colon such that the tip was 4 cm proximal to the anus. The TNBS, dissolved in 50% ethanol was slowly administered into the lumen of the colon via the catheter fitted onto a 1 ml syringe.

B. Treatment with pCMV-TGF-β Prevents Colitis.

Mice treated with TNBS to induce colitis were divided into 2 groups. The first group received no treatment (i.e., control group). The second group was lightly anesthetized with metophane (methoxylflurance, Schering-Plough) and given 20 μl of PBS containing 100 μg of plasmid DNA intranasally. The quality of plasmid DNA was verified by electrophoresis on 1% agarose gel just prior to administration. Two additional control groups were included. These animals did not receive TNBS. The first control group was given only ethanol (no TNBS). The second group control group was given only the p-CMV-TGF-β plasmid (p-CMV-TGF-β was prepared as described in Example 1). The weight of each mouse in the four groups described above was monitored every 24 hours for seven days.

Figure 4:
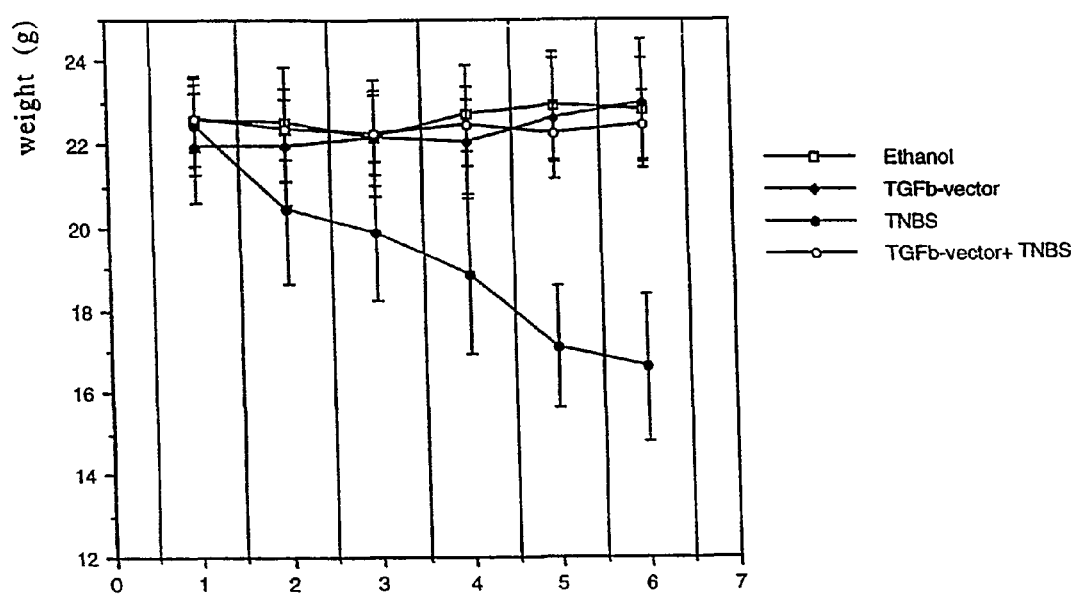
FIG. 4 shows the weight changes of mice following treatment with pCMV-TGF-β1 for seven days post-treatment in one embodiment of the present invention, as well as untreated mice with TNBS-induced colitis.

FIG. 4 shows the weight of mice in all four groups for 7 days post treatment. The two control groups not treated with TNBS (i.e, ethanol and TGF-β containing vector) maintained their weight at or above their weight on day zero. The mice given TNBS and no treatment manifested continuous weight loss over the entire treatment period. However, mice with TNBS colitis treated with the p-CMV-TGF-β plasmid maintained their weight at or near the levels of the control groups.

Figure 5:
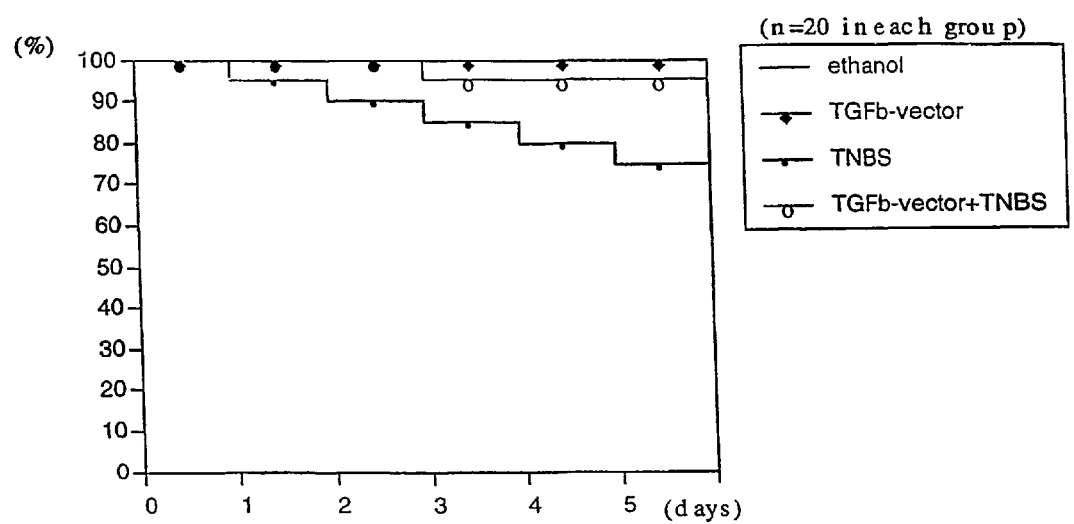
FIG. 5 shows the rate of survival of mice following treatment with pCMV-TGF-β1 for seven days post-treatment in one embodiment of the present invention.

FIG. 5 shows the survival of mice in the above four groups. The survival rate was monitored for 5 days post-treatment. The two control groups not treated with TNBS (Ethanol and TGF-β containing vector) maintained near 100% survival. The mice given TNBS and no treatment showed a decreased survival rate of near 75%. However, mice with TNBS colitis treated with the p-CMV-TGF-β plasmid had a survival rate at or near the levels of the control groups.

C. Treatment of Active Colitis with p-CMV-TGF-β and rTGF-β1 Protein

In these experiments, mice were administered 1.5-2.0 mg of TNBS in 45% ethanol as described above to induce colitis. Administration was on day −7. As shown in FIG. 6, 7 days after administration the mice were losing weight rapidly. At this point, the mice were split into three groups. The first group received no treatment. The second group received intranasal administration of p-CMV-TGF-β as described above in section B. The third group was administered 5 μg of rTGF-β1 (purchased from R&D) per day for three days. Protein was administered via intraperitoneal injection. FIG. 6 shows that mice administered p-CMV-TGF-β exhibited weight gain back to their original weight within 5 days following treatment. The mice given rTGF-β1 did not regain any lost weight. Mice given no treatment continued to lose weight.

These experiments demonstrated that intranasal administration of p-CMV-TGF-β resulted in both prevention of the onset of symptoms of TNBS colitis in mice and treatment of ongoing colitis. This is in contrast to mice administered rTGF-β1 protein, which did not result in effective treatment of colitis.

EXAMPLE 4

Histologic Assessment of Tissues

In this Example, tissues from the mice tested in Example 3 above, were examined. Colonic tissues were obtained 7 days after treatment with TNBS to induce colitis as described in Example 3. Samples were also obtained from mice treated with p-CMV-TGF-β. Samples were fixed in 10% buffered formalin phosphate (Sigma-Aldrich), embedded in paraffin, cut into sections, and stained with hematoxylin and eosin. Stained colon sections were examined for evidence of colitis using histologic criteria previously described (Neurath et al., J. Exp. Med., 182:1281 [1995]). The level of inflammation observed in the samples was graded on a scale from 0-4 (0, no signs of inflammation; 1, very low level; 2, low level of leukocyte infiltration; 3, high level of infiltration, high vascular density, and thickening of the colon wall; 4, transmural infiltrations, loss of goblet cells, high vascular density, and thickening of the colon wall).

Results of the histologic assessment of the mice of Example 3B are shown in Table 2. Table 2 shows the number of mice in each group exhibiting each grade of inflammation. As indicated, mice in the control groups receiving only ethanol or only p-CMV-TGF-β were graded at a low level of inflammation. Mice receiving only TNBS and no treatment were primarily graded at high levels of inflammation. Mice treated with p-CMV-TGF-β were primarily graded at low levels of inflammation. These results correlate with the weight and survival in demonstrating that treatment with p-CMV-TGF-β prevents symptoms of TNBS induced colitis.

Table 3 shows the results of histological assessment based on grade of infection of the mice of Example 3C. As indicated, untreated mice and mice treated only with rTGF-β1 protein were graded at high levels of inflammation. Mice treated with p-CMV-TGF-β were graded at low to intermediate levels of inflammation. These results correlate with the results of Example 3C in demonstrating that p-CMV-TGF-β and not rTGF-β1 protein is an effective treatment for TNBS induced colitis.

TABLE 2

Histological Assessment of Mice Treated With p-CMV-TGF-β

| Grade | p-CMV-TGF-β + TNBS | TNBS Only | Ethanol | p-CMV-TGF-β |
|---|---|---|---|---|
| 0 | 2 | 0 | 5 | 5 |
| 1 | 3 | 0 | 0 | 0 |
| 2 | 0 | 0 | 0 | 0 |
| 3 | 0 | 2 | 0 | 0 |
| 4 | 0 | 3 | 0 | 0 |

TABLE 3

Histological Assessment of Mice Treated with rTGF-β or p-CMV-TGF-β

| Grade | No Treatment | rTGF-β1 protein | p-CMV-TGF-β |
|---|---|---|---|
| 0 | 0 | 0 | 2 |
| 1 | 0 | 0 | 5 |
| 2 | 0 | 2 | 2 |
| 3 | 2 | 2 | 0 |
| 4 | 4 | 2 | 0 |

EXAMPLE 5

PCR Detection of pCMV-TGF-β in Mice

This Example describes the detection of pCMV-TGF-β specific DNA and RNA in mouse tissue. Mice were treated with TNBS to induce colitis and pCMV-TGF-β using the method described in Example 3 above. DNA and RNA were isolated from lung, colon, and spleen tissues on 5, 14, and 28 days following administration of TNBS and pCMV-TGF-β. DNA was directly used in a PCR (DNA-PCR) reaction and RNA was used in RT-PCR.

Tissue DNA was isolated by a DNA isolation kit (Gentra Systems). Tissue RNA was isolated by standard guanidinium isothiocyanate extraction method, followed by the treatment with RQ-1 RNAse-free DNAse (Promega).

PCR was used to amplify TGF-β DNA and RNA as well as GAPDH mRNA (used as an internal control for the PCR reaction). Primers used for PCR reactions were: 5' primer (22 mer) 5'-AGAAGTTGGTCGTGAGGCACTG-3' (SEQ ID NO:3), derived from the 5' sequence of synthesized splicing site upstream of TGF-β cDNA, and 3' primer (22 mer), 5'-GAGCTCCGACGTGTTGAACAG-3' (SEQ ID NO:4), derived from the sequence within the pCMV-TGF-β cDNA in the plasmid. The splice site facilitated the distinction of the sizes between DNA-PCR and RT-PCR of pCMV-TGF-β. For GAPDH, the primer sequences used were 5' primer (24 mer): 5'-GTCTTCACCACCATGGAGAAGGCT-3' (SEQ ID NO:5), 3' primer (23 mer): 5'-CATGCCAGTGAGCTTC-CCGTTCA-3' (SEQ ID NO:6). PCR was performed using thermal cycler set for 30 cycles of 94° C. for 45 sec, 60° C. for 60 sec, 72° C. for 90 sec and final extension at 72° C. for 10 min. Amplified products were visualized on a 2% agarose gel.

The TGF-β plasmid DNA is still detectable by DNA-PCR in lung, colon and spleen tissues 28 days following intranasal administration of pCMV-TGF-β. The TGF-β mRNA was still able to be detected in all three tissues 14 days after intranasal administration of pCMV-TGF-β.

These results demonstrate two important findings: 1) TGF-β DNA is present in tissues following intranasal administration of pCMV-TGF-β; and 2) TGF-β mRNA is expressed in tissues following intranasal administration of pCMV-TGF-β.

EXAMPLE 6 pCMV-TGF-β Induces T-Cells to Secrete High Levels of TGF-β and Low Levels of IFN-γ

In this Example, cytokine secretion by colonic lamina propria T-cells of the mice of Example 3 was assayed. The levels of secretion of the cytokines TGF-β and IFN-γ was measured in the control and experimental mice of Example 3.

A. Isolation and Culture of Lamina Propria (LP) T-Cells and Macrophages.

Lamina propria mononuclear cells (LPMC) were isolated from lamina propria using the technique of Van der Heijden and Stok (Van der Heijden and Stok, J. Immunol. Meth., 103:161-167 [1987]). The colonic specimens were first washed in HBSS-calcium magnesium free and cut into 0.5 cm pieces. They were then incubated twice, each time for 15 min in HBSS containg EDTA (0.37 mg/ml) and dithiothreitol (0.145 mg/ml) at 37° C. The specimens were further digested in RPMI containing collagenase D (400 U/ml) and DNase I (0.01 mg/ml) (both obtained from Boehringer Mannheim). The LP cells released from the tissue were then resuspended in 100% Percoll, layered underneath a 40% Percoll gradient (Pharmacia Biotech) and spun at 1800 rpm to obtain the lymphocyte-enriched population accumulating at the 40-100% interface.

The resultant LPMC were plated on a plastic surface for separation into adherent and non-adherent cell populations. Mouse CD4$^+$ T-cell purification columns (R&D) were used to purify T-cells. The resultant cell populations were shown by flow cytometry (FACScan; Becton Dickinson) to contain greater than 85% CD4$^+$ T-cells.

The lamina propria T-cells obtained were suspended in complete medium consisting of RPMI 1640 supplemented with 3 mM L-glutamine, 10 mM HEPES buffer, 10 μg/ml gentamycin, 100 U/ml each of penicillin and streptomycin (Life Sciences), 0.05 mM 2-ME and 10% heat-inactivated FCS (Life Sciences) and cultured at a concentration of 1×10$^6$ cells/ml in 24-well culture plates (Costar) with or without stimulation. Stimulation was accomplished by plate-bound anti-CD3ε (clone 145-2C11, Pharmingen), precoated at 10 μg/ml anti-CD3ε in carbonate buffer (pH 9.5) overnight at 4° C.) and soluble anti-CD28 (1 mg/ml, clone 37.51, Pharmingen) for 48 hours.

The adherent cell population (LP macrophage-enriched cells, which were shown by flow cytometry to contain 70% F4/80-positive cells and 25% N418-positive cell population) was also cultured. These cells were cultured at a concentration of 1×10$^6$ cells/ml and stimulated overnight (18 hours) with 1000 u/ml IFN-γ (R&D) and then with SAC at a 1:10,000 dilution (Pansorbin, Calbiochem) for an additional 24 hours.

B. Cytokine Secretion Assays

For measurement of TGF-β1 secretion, cells were cultured in serum-free medium supplemented with 1% nutridoma-SP (Roche) for 60 h as previously described (Boirivant et al., J. Exp. Med., 188:1929 [1998]).

Supernatants of cell cultures were collected and assayed for cytokine production by ELISA. IFN-γ was assayed by mini-kit (Endogen). TGF-β1 was assayed using the Max TGF-β assay kit (Promega) after the treatment of sera or serum-free supernatants with 1M HCl, followed by the NaOH neutralization. Optical densities were measured on a ELISA reader (MR 5000: Dynatech Labs) at a wavelength of 490 nm as previously described (Neurath et al., J. Exp. Med., 182:1281 [1995]; Boirivant et al., J. Exp. Med., 188:1929 [1998]; Neurath et al., J. Exp. Med., 183:2605 [1996]).

The results are shown in FIG. 7. As indicated, control mice not treated with TNBS exhibited low levels of both TGF-β and IFN-γ secretion. Mice given TGF-β alone exhibited little IFN-γ secretion and moderate TGF-β secretion. T-cells from mice administered TNBS alone or TNBS and the control vector and having active colitis manifested high levels of IFN-γ secretion and low levels of TGF-β secretion. In addition, these cells stimulated with SAC plus IFN-γ produced large amounts of IL-12 p70 and low amounts of TGF-β1. Similarly, cells from mice administered TNBS that also received intranasal pTet-on-TGF-β1, but not doxycycline, produced high levels of IFN-γ and IL-12, but not low amounts of TGF-β1.

These results were in striking contrast to those obtained with LPMC from mice that received TNBS, intranasal pTet-on-TGF-β1 and doxycycline. In this case, the splenocytes produced low amounts of IL-12/IFN-γ and large amounts of TGF-β1. The TGF-β1 was secreted in a largely active form, since about 90% of the total TGF-β1 detected by ELISA could be detected in the absence of acidification of the culture supernatant. Moreover, TGF-β secretion was detected in unstimulated cells from this mouse group presumably due to in vivo cell activation by TNP-haptenated protein. Taken together, these experiments show that a reciprocal relation exists between IL-12/IFN-γ and TGF-β1, with high levels of the former and low levels of the latter associated with inflammation (the reverse was true in the absence of inflammation).

In addition, the production of IL-10 was also measured for the same anti-CD3ε/anti-CD28-stimulated LPMC populations. As also shown in FIG. 7, while TNBS-colitis induction in the absence of intranasal administration of pTet-on-TGF-β1 was associated with cells exhibiting a modest rise in IL-10 production, mice treated with TNBS-colitis and treated with intranasal pTet-on-TGF-β1 and doxycycline yielded cells exhibiting massive IL-10 secretion. This observation was in agreement with previous experiments conducted with pCI-TGF-β1, in that intranasal administration of the latter plasmid also resulted in massive IL-10 secretion.

This Example illustrates that administration of TGF-β in pCMV-TGF-β affects the secretion of TGF-β, IFN-γ, and interleukins by T-cells.

EXAMPLE 7 pTetCMV-TGF-β Prevents Symptoms of TNBS Colitis in Mice

The studies described in this Example were designed to test the ability of the inducible plasmid, pTetCMV-TGF-β1 ("pTet-on-TGF-β1) (described in Example 2) to prevent TNBS colitis.

Pathogen free, 5-6 week old male SJL/J mice (described in Example 3) were used in this study. On day minus 7 (relative to TNBS administration), mice lightly anesthetized with metophane (methoxylflurance, Schering-Plough) were administered twenty μl of PBS containing 100 μg of plasmid DNA (either pTet-on-TGF-β1 or pTet-on mock) intranasally. The quality of plasmid DNA was verified by electrophoresis on 1% agarose gel just prior to administration. On day minus 3, the mice were split into two further groups, one group received doxycycline (500 μg I.P.) to induce production of TGF-β1, while one group did not receive doxycycline. On day zero, the mice were treated with a single intra-rectal dose of TNBS (2.5 mg) dissolved in ethanol to induce TNBS-colitis.

Figure 8:
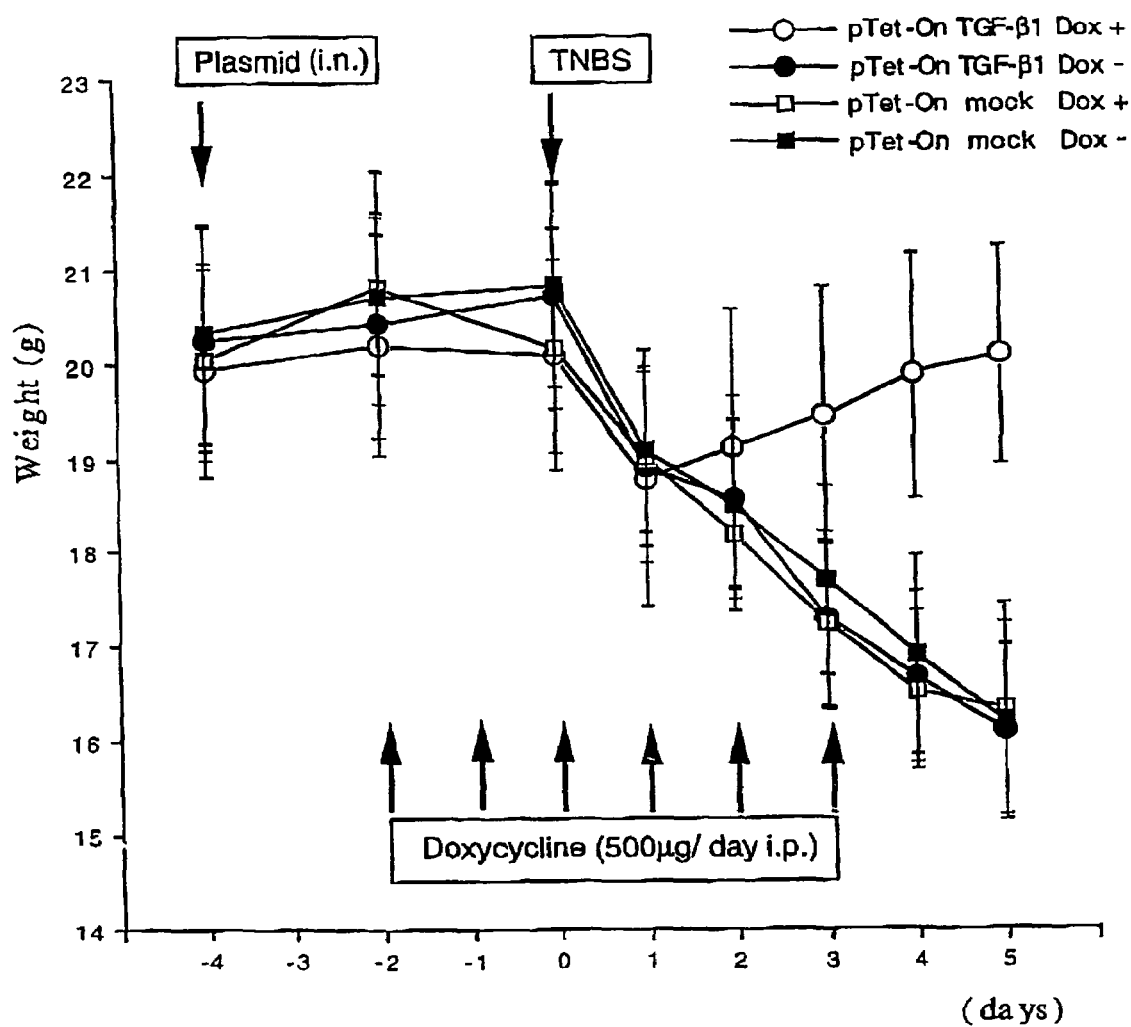
FIG. 8 provides a graph showing the weight of mice measured over time, following treatment with pTet-on-TGF-β1 in one embodiment of the present invention.

FIG. 8 shows the weight of mice from days −4 to +5. The group of mice not administered doxycycline (and thus not producing TGF-β1) exhibited rapid and severe weight loss following induction of TNBS colitis. In contrast, mice given pTet-on-TGF-β1 and doxycycline (thus inducing the production of TGF-β1) exhibited only small amounts of weight loss.

Tissues from the mice were also assayed for histological symptoms of inflammation as described in Example 4. The results are shown in Table 4. Mice treated only with pTet-CMV-TGF-β1 and not given doxycycline to induce expression of TGF-β1 were primarily graded at high levels of inflammation. Indeed, mice given pTet-on-TGF-β1 without doxycycline, mock pTet-on without doxycycline, and pTet-on with doxycycline exhibited severe colitis, marked by transmural leukocyte infiltration, loss of goblet cells, and severe thickening of the colonic walls. Mice given pTet-CMV-TGF-β1 and doxycycline were primarily graded at low levels of inflammation. Indeed, these animals exhibited normal colonic histopathology, except for a slight thickening of the serosal connective tissue.

The results of this experiment demonstrate two important findings. The first is that the plasmid pTetCMV-TGF-β1 allows inducible control of the expression of the TGF-β1 gene. Expression of the gene can be turned on at will by the administration of doxycycline. Second, not only can the expression of TGF-β1 prevent colitis when given concurrently with TNBS (shown in Example 3), the expression of TGF-β1 can also prevent the onset of colitis when given before TNBS.

TABLE 4

Histological Assessment of Mice Treated with pTet-CMV-TGF-β1

| Grade | pTet-CMV-TGF-β1 + Doxycycline | pTet-CMV-TGF-β1 |
|---|---|---|
| 0 | 1 | 0 |
| 1 | 2 | 0 |
| 2 | 2 | 0 |
| 3 | 0 | 1 |
| 4 | 0 | 4 |

EXAMPLE 8 pTetCMV-TGF-β1 Induces T-Cells to Secrete High Levels of TGF-β1

In this Example, experiments to determine cytokine secretion by splenic lymphocytes from the mice of Example 7 are described. The secretion of TGF-β1 was assayed in mice not treated with doxycycline as well as mice treated with doxycycline. Splenic T-cells were isolated by methods described in the art (Boirivant et al., J. Exp. Med., 188:1929 [1998]). Spleens were aseptically removed. Cells were dispersed in 1× PBS by applied pressure to spleen tissue. The dispersed splenocytes were then filtered through a 100 μM filter and depleted of RBCs by hypotonic lysis with ACK lysing buffer (Biofluids Inc) using standard methods. The cells were then resuspended in 100% Percoll, layered underneath a 40% Percoll gradient (Pharmacia Biotech) and spun at 1800 rpm to obtain the lymphocyte-enriched population accumulating at the 40-100% interface. T-cells were further purified using mouse CD4+ T-cell purification columns (R&D). The resultant cell populations were shown by flow cytometry (FACScan; Becton Dickinson) to contain greater than 90% CD4+ T-cells. TGF-β1 secretion was measured as described in Example 6. Secretion was measured in both unstimulated and anti-CD3/CD28 stimulated T-cells.

Figure 9:
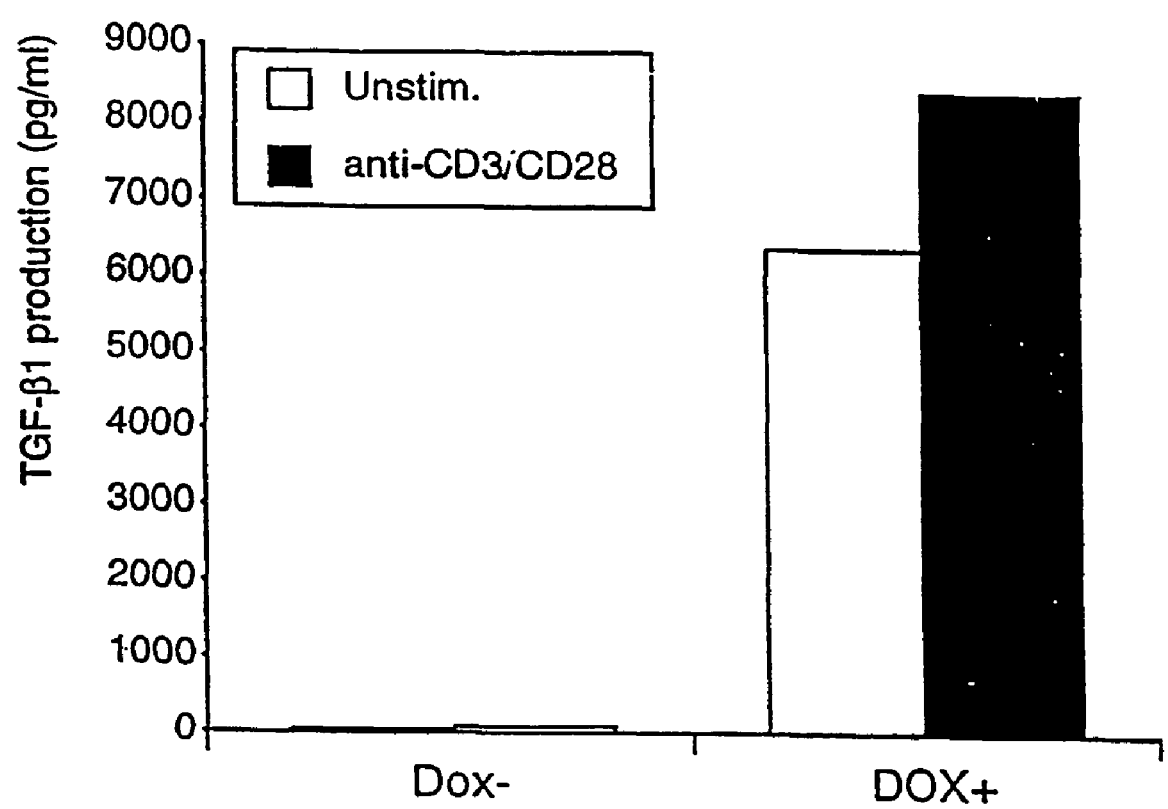
FIG. 9 shows levels of TGF-β1 secretion by colonic lamina propria T-cells of mice in one embodiment of the present invention.

The results are shown in FIG. 9. As indicated, the mice given doxycycline produced a large amount of TGF-β1, while those not given doxycycline produced limited amounts. This experiment directly demonstrates that the intranasal administration of pTetCMV-TGF-β1 followed by induction of expression by doxycycline results in the secretion of TGF-β1 by spleen T-cells.

EXAMPLE 9

Expression of β-Galactosidase

This Example demonstrates that the vectors described above can be used to monitor the expression of a reporter gene, (e.g, β-galactosidase), in host tissues of mice with TNBS colitis given pCMV-β-Gal intranasally. Confocal immunofluorescence was used to detect the presence of β-galactosidase and CD3+, CD4+, or CD11b+ (i.e., markers for T-cells or macrophages) in tissue samples.

Colitis was induced in mice as described in Example 3. Mice were given 100 μg of pCMV-β-Gal (pCMV-TGF-β (Example 1) with the β-galactosidase gene replacing TGF) intranasally and sacrificed 5-7 days later.

Spleen and colon tissues were isolated and put into OCT compound on dry ice, and 5-μm cryosections were cut. Dual immunofluorescence was performed to determine co-localization of intracellular β-galactosidase and cell surface markers as follows. Sections were fixed in cold acetone and then rehydrated in PBS, then the sections were exposed to 5% goat serum and hamster anti-Fc blocking mAb (1:100 dilution, Pharmingen) in PBS for 20 min to block non-specific antibodies of fluorochrome. The sections were then treated with rabbit anti-β-galactosidase antibody (1:1000 dilution, Chemicon) for 40 min, followed by treatment with Texas Red-conjugated goat-anti rabbit antibody (Jackson Immuno) and FITC-conjugated anti-CD3 for 40 min; 4). Finally, sections were mounted and analyzed by Confocal immunofluorescence using a Leica TCS-NT/SP confocal microscope (Leica Microsystems) using a 40× objective, NA 1.2. Fluorochromes were excited using an argon laser at 488 nm for FITC, and a krypton laser at 568 nm for Texas Red. DIC images were collected simultaneously with the fluorescence images using the transmitted light detector. Images were processed using the Leica TCS-NT/SP software (version 1.6.551).

The results show that β-galactosidase was detected in CD3+CD4+ T-cells in spleen and CD3+ T-cells and CD11b+ macrophages in the colon. This experiment demonstrates that genes are expressed from the vectors of the current invention in spleen and macrophage cells.

EXAMPLE 10 pTet-on-TGF-β1 In Vitro Transfection and Western Blotting of rtTA

In this Example, experiments involving the in vitro transfection of pTet-on-TGF-β1 and Western blotting of rtAT are described. pTet-on-TGF-β1 was transfected into COS-7 cells using lipofectamine 2000 (Life Technologies) diluted in opti-MEM I (Life Technologies), and cultured in 5 ml Iscove's MEM containing 3% FCS, with or without doxycycline (1 μg/ml), in 60 mm culture dishes. Three days after transfection, the supernatant present in each dish was collected and the amount of active TGF-β1 in the supernatant was assayed by ELISA.

At the same time, COS-7 cell lysates were prepared by exposing the cells to 10 mM Tris-HCl/150 mM NaCl buffer containing 1% Nonidet P-40, protease inhibitor cocktail (Boehringer Mannheim), and 0.5% sodium deoxycholate. Pre-determined equal amounts of the cell lysates obtained were loaded onto 10% SDS-PAGE gels, subjected to electrophoresis, and transferred onto Hybond ECL nitrocellulose membranes (Amersham Pharmacia Biotech.). The membranes were blocked with TBS buffer containing 5% milk and 0.05% Tween-20, and incubated for 3 hours with 1:200 diluted rabbit anti-VP16 (Clontech), which recognizes the VP16 domain of rTA protein. The membranes were washed three times with 0.1% Tween-TBS, and incubated with secondary antibody (1:1000 diluted peroxidase-conjugated anti-rabbit IgG) for 1 hour. After washing 3 times, bound anti-VP16 was visualized using the ECL Plus kit (Amersham Pharmacia Biotech.).

EXAMPLE 11

Doxycycline Induction of TGF-β1 by Intranasal Administration of pTet-CMV-TGF-β1 In Vivo In this Example, experiments conducted to assess doxycycline induction of TGF-β1 by pTet-CMV-TGF-β1 in vivo are described. pTet-CMV-TGF-β1 was administered intranasally to test SJL/J mice (100 μg/mouse). Beginning two days later, 500 μg doxycycline were given to each mouse for four days by intraperitoneal injection. Each day after cessation of doxycycline administration and up to four further days, the mice were sacrificed in order to obtain splenocytes for culture with immobilized anti-CD3ε and soluble anti-CD28, to assess their ability to produce active TGF-β1. After sacrifice, spleen mononuclear cells were stimulated with anti-CDε/anti-CD28 without doxycycline for 60 hours in vitro, and assessed by ELISA.

Figure 10:
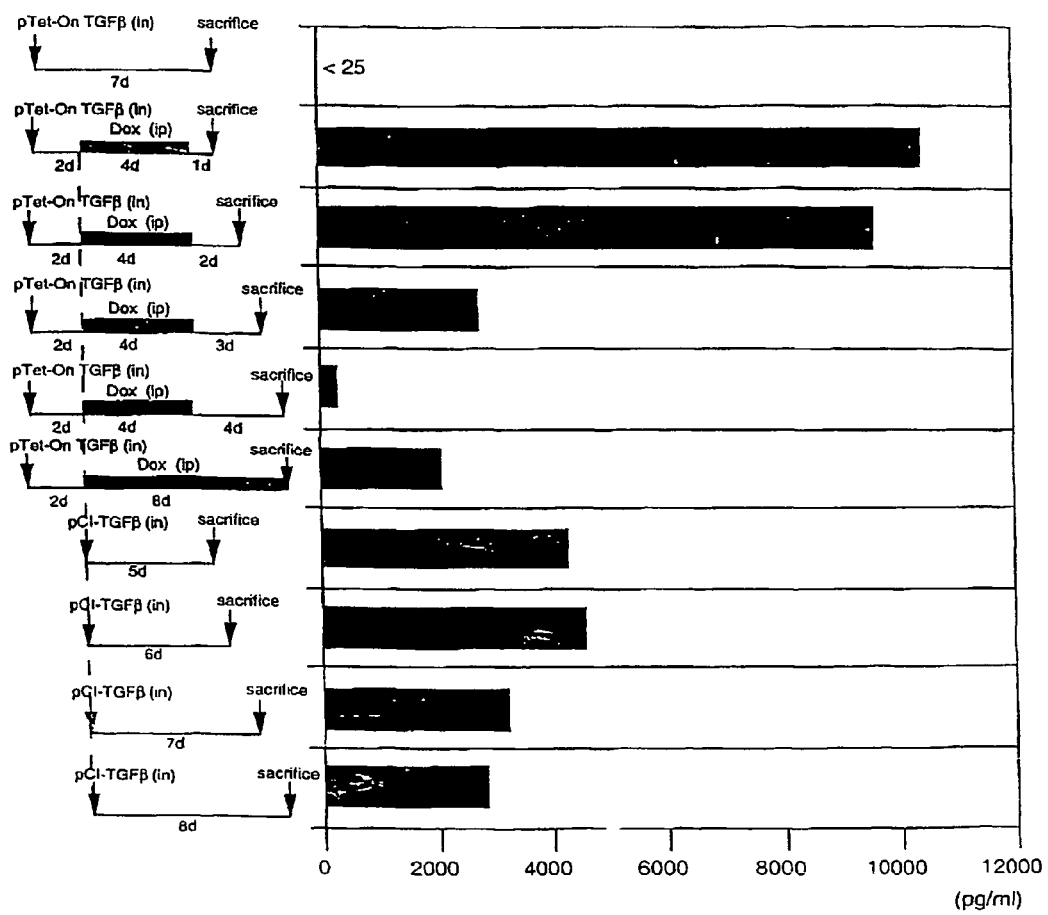
FIG. 10 shows the tight control and large amount of active TGF-β1 produced by spleen mononuclear cells after intranasal administration of pTet-CMV-TGF-β1 in SJL/J mice with TNBS colitis.

As shown in FIG. 10, two days after cessation of doxycycline administration, cells from mice given pTet-CMV-TGF-β1 plus doxycycline (DOX), produced massive amounts of TGF-β1 (8,600 to 14,800 pg/ml), whereas cells from mice given an equal dose of non-regulatable TGF-β1 plasmid (pCI-TGF-β1) produced considerably lower amounts of TGF-β1 (700 to 4,600 pg/ml). Since preliminary experiments indicated that the presence of doxycycline in the cultures did not influence TGF-β1 production by cultured splenocytes, doxycycline was not added to the cultures. Thus, the production of TGF-β1 by cells following stimulation in vitro represented TGF-β1 induced by doxycycline in vivo.

As also shown in FIG. 10, the production of TGF-β1 by splenocytes quickly returned to baseline levels three to four days after cessation of doxycycline administration, as compared to production by splenocytes from mice that continued to receive doxycycline, or as compared to production by splenocytes from mice that received non-regulatable pCI-TGF-β1. Taken together, these results indicate that TGF-β1 production induced by giving intranasal pTet-on-TGF-β1 (i.e., pTet-CMV-TGF-β1) is tightly controlled by doxycycline administration in vivo. In addition, these results show that mice administered pTet-CMV-TGF-β1 exhibit essentially no TGF-β1 production in vivo in the absence of doxycycline. Although an understanding of the mechanism is not necessary in order to use the present invention and it is not intended that the present invention be limited to any particular mechanism, it is believed that these results are probably due to the fact that in the plasmid construct used, the two transcription units (rtTA-V16 and TGF-β1) are oriented in the opposite directions and flanked by poly A sites in both ends. Thus, non-TRE-driven TGF-β1 mRNA transcription leaking from the plasmid is subtracted by constitutive transcription of rtTA-RNA driven by the CMV promoter in the opposite directions.

Figure 11:
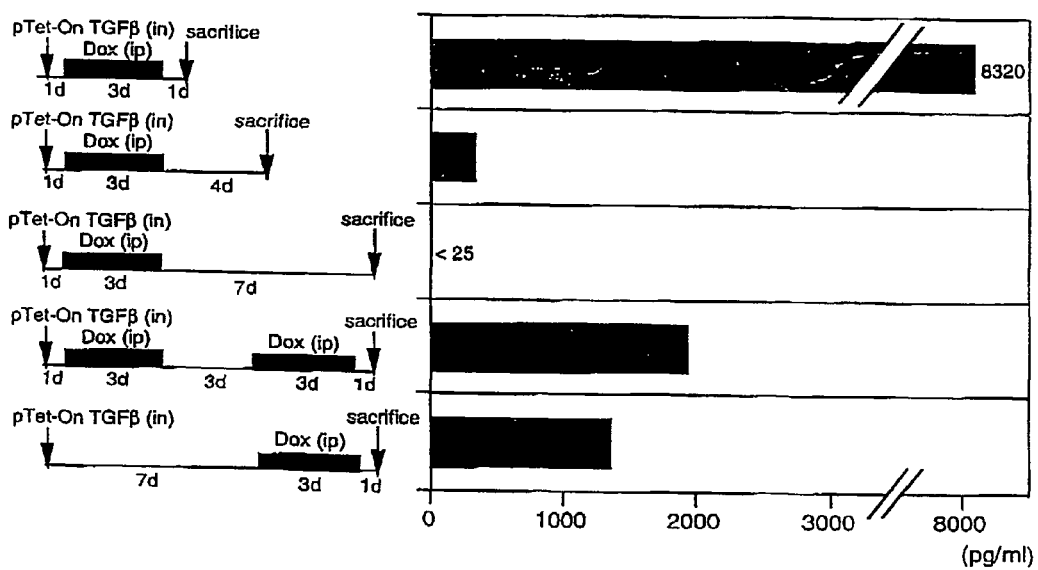
FIG. 11 shows the effects of interrupted doxycycline administration on TGF-β1 production.

In additional experiments, the effect of interrupted doxycycline administration on TGF-β1 production was examined in order to determine whether plasmid-derived TGF-β1 production can be restored following initial doxycycline withdrawal. As indicated in FIG. 11, 3 days after administration of doxycycline to mice previously administered intranasal pTet-on-TGF-β1, splenocytes produced large amounts of TGF-β1. However, 3 days later, after cessation of doxycycline administration, production of TGF-β1 had fallen to baseline levels. Then, after 3 further days of doxycycline administration, cells again produced considerable amounts of TGF-β1, while cells from mice not given a second doxycycline dose produced no TGF-β1. This on-off-on doxycycline administration schedule, which leads to serial induction and cessation of TGF-β1 production provides further proof that the administration of pTet-on-TGF-β1 is indeed regulatable by doxycycline in vivo.

EXAMPLE 12

Treatment Effect of pTet-CMV-TGF-β1 in Established TNBS-Colitis

In this Example, experiments conducted to determine whether colitis could be reversed are described. In these experiments, the effect of intranasally administered pTet-CMV-TGF-β1 on TNBS-colitis was examined. Thus, SJL/J mice were administered TNBS per rectum (1.5 mg/mouse) to induce TNBS-colitis, as described above. At day 7 after establishment of colitis, the mice received a single dose of intranasal pTet-CMVTGF-β1, along with five consecutive daily injections of doxycycline (500 μg/day) by intraperitoneal injection. As colitic mice refused water containing doxycycline and use of doxycycline-containing food does not allow an accurate assessment of doxycycline consumption, intraperitoneal administration of doxycycline was used. In addition, intraperitoneal administration of doxycycline allows observation of wasting due to colitis, not refusal of food or water.

Figure 12:
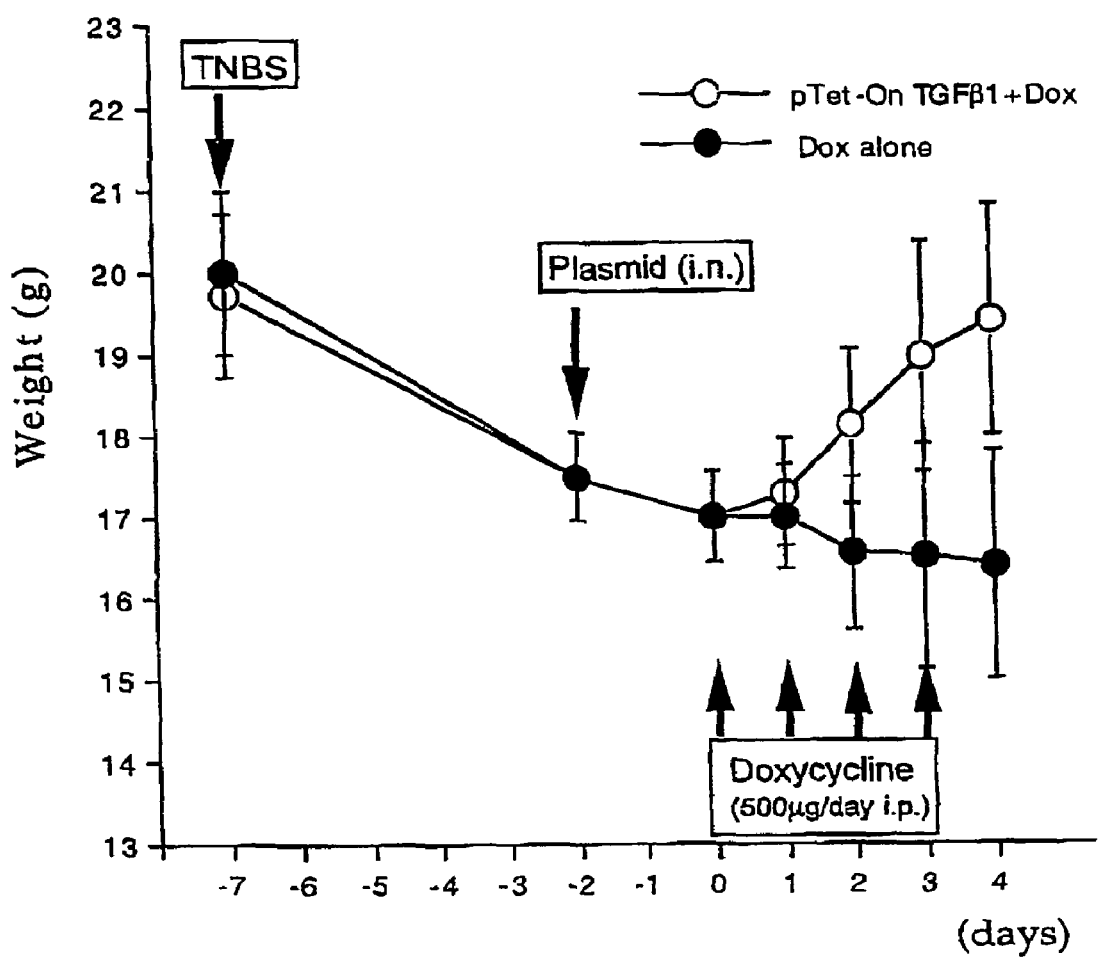
FIG. 12 provides results showing that the intranasal administration of pTet-CMV-TGF-β1 abrogates established TNBS-colitis in SJL/L mice with concomitant doxycycline treatment.

Each group of 15 mice were administered TNBS at day −7, then treated with or without intranasal pTet-CMV-TGF-β1 (100 μg/mouse) at day −2, followed by intraperitoneal injection of doxycycline (500 μg/day), started at day 0, for 4 or 5 days. Weight changes of mice in one experiment (mean±SD), representative of three independent experiments are indicated in FIG. 12. In FIG. 12, the open circles (○) indicate pTet-CMV-TGF-β1 plus doxycycline, while the filled circles (●) indicate doxycycline alone. As shown in FIG. 12, mice treated with intranasal pTet-CMV-TGF-β1 plus doxycycline manifested a striking reversal of weight loss, accompanied by an improvement in coat appearance, activity, and almost complete resolution of macroscopic and microscopic evidence of colitis. Thus, the lack of weight loss in this group correlated with histologic examination of colonic tissue. Splenocytes from mice treated with pTet-CMV-TGF-β1 plus doxycycline exhibited decreased IFN-γ and IL-12 production, as compared to mice not given doxycycline. In addition, intranasal administration of pTet-CMV-TGF-β1 plus doxycycline led to greatly increased TGF-β1 production. In parallel with results obtained during administration of pTet-CMV-TGF-β1 with doxycycline to mice during initial induction of TNBS-colitis, administration of plasmid in established colitis led to LPMC manifesting increased IL-10 production.

EXAMPLE 13

Bleomycin Treatment, Fibrosis Induction and Assessment

In this Example, experiments were conducted using C57BL/6J mice anesthetized by intraperitoneal injection of 150 ml of a ketamine-HCl (Fort Dodge) and xylazine-HCL (Butler) combination diluted in PBS. Pulmonary fibrosis was induced in mice (6-8 weeks old) by a single intra-tracheal instillation of bleomycin hydrochloride (Calbiochem), at a dose of 0.15 U in a final volume of 50 µl, using a 25 gauge needle. Concomitantly, mice received doxycycline (i.p.) for 5 days subsequently to pTet-on-TGF-β1 or pTet-mock intranasal administration. Mice were maintained for 2-3 weeks prior to sacrifice.

Lungs were perfused in situ through the right ventricle with saline, and then inflated and fixed with 10% buffered formalin after harvest from treated mice. Lungs were ligated at the bronchi, excised, further fixed by immersion in 10% buffered formalin for at least 24 hours before paraffin embedding, sectioning, and staining with hematoxylin and eosin (H&E) or trichrome.

Alveolar thickness and fibrosis were scored in 10 random fields at three levels through each lung, using methods known in the art (See, Ashcroft, J. Clin. Pathol., 41:467-470 [1988]), by a histopathologist blinded to the treatment groups (i.e., controls versus test animals).

In addition, the total lung collagen content of treated animals was determined by assaying total soluble collagen, using the Sircol Collagen Assay kit (Biocolor), according to the manufacturer's directions. Briefly, right lungs were harvested at day 14 to 21 after bleomycin administration and homogenized in 10 ml 0.5 M acetic acid containing about 1 mg pepsin/10 mg tissue residue. Each sample was incubated for 24 hours at 4° C., with stirring. After centrifugation, 200 µl of each supernatant was assayed. One milliliter of collagen-binding Sircol dye reagent was added to each sample and then mixed for 30 minutes. After centrifugation, the pellet was suspended in 1 ml of the alkali reagent included in the kit, and read at 540 nm by a spectrophotometer. Acid soluble Type I collagen supplied with the kit was used to generate a standard curve. Sircol dye binds specifically to hydroxyproline (i.e., $[Gly-X-Y]_n$ helical structures of Types I to V collagens, and also possibly types VI to XIV. Since all collagens contain about 14% hydroxyproline by weight, the collagen content values obtained with this method provides an indication of total collagen content.

Figure 13:
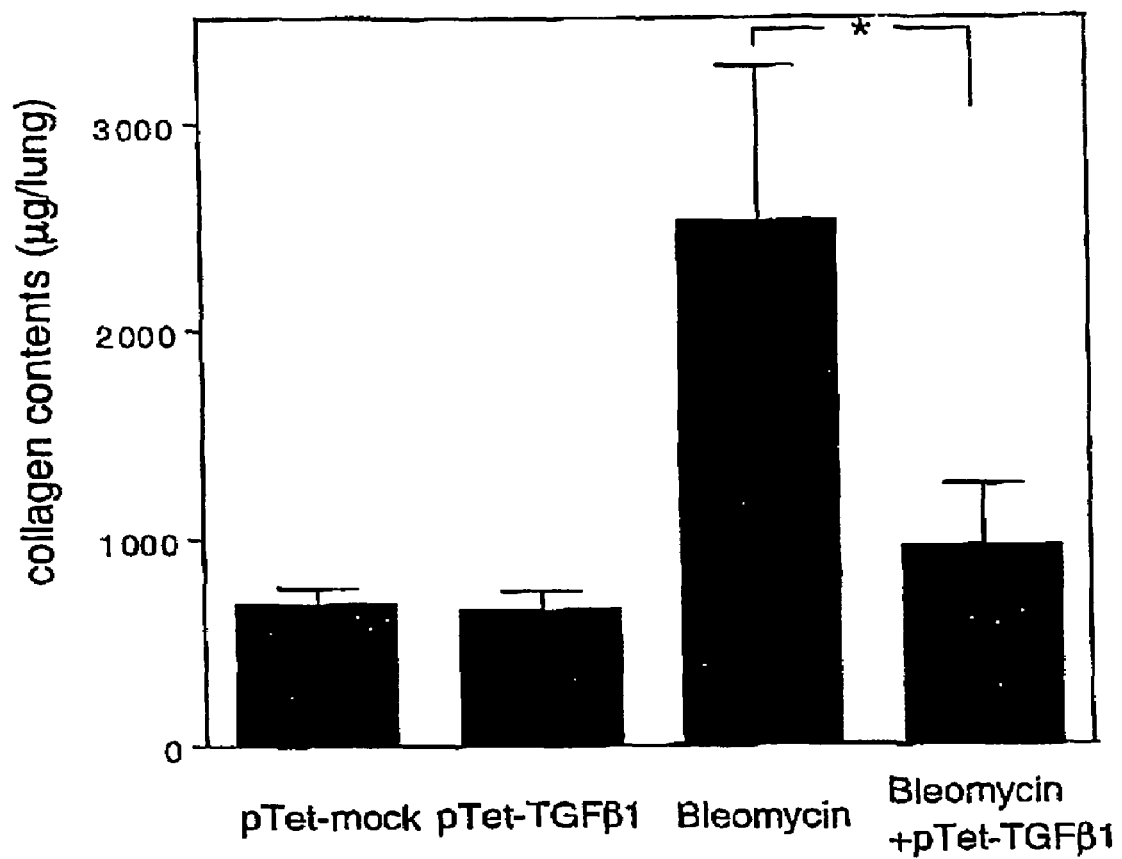
FIG. 13 provides results showing the lung collagen content of mice treated with pTet-CMV-TGF-β1, bleomycin, and/or doxycycline.

At day 21 after instillation of bleomycin, whole right lung contents in mock vector treated (p-Tet-on-mock) (i.e., control) mice and bleomycin-challenged mice treated with or without pTet-CMV-TGF-β1 and doxycycline were determined. As indicated in FIG. 13, intranasal pTet-CMV-TGF-β1 in combination of doxycycline (intraperitoneal) did not increase the collagen content in lungs. Indeed, the combination protected animals against the increase in collagen content typically observed in bleomycin-induced fibrosis. In this Figure, representative results are shown from three independent experiments consisting of 9 mice in each group. Statistical significance with $p<0.05$ is indicated with an asterisk in this Figure.

EXAMPLE 14

Method for Treatment of IBD Patients with Plasmids Expressing TGF-β

In this Example, methods for treating patients with IBD are described. It is contemplated that IBD in humans be treated with a TGF-β expressing plasmid such as pTet-CMV-TGF-β1. Patients with IBD are treated with 2-20 mg of plasmid administered via the intranasal route by nasal spray or nebulizer of saline or in an organic solvent in which the DNA is dissolved. The plasmid DNA is administered either once or multiple times, as desired. The preferred outcome is a clinical effect in which substantial elimination of symptoms of IBD is obtained. If the preferred outcome is not obtained after a single dose of the plasmid, multiple doses are administered. High doses of plasmid DNA, such as 10-100 mg may also be administered if the preferred outcome is not obtained using the range described above. If symptoms of IBD re-occur (a non-desirable outcome), the plasmid is re-administered until substantial elimination of the symptoms results. In this manner, the plasmid is re-administered when relapse of symptoms occurs.

In some embodiments, pTet-CMV-TGF-β1 is intranasally administered in order to deliver a plasmid under the control of doxycycline. In this case, the patient is also treated with oral doxycycline in order to activate the plasmid. In separate studies, it was found that a dose of 100 µg doxycycline per mouse is sufficient to activate the Tet-on gene in a transgenic mouse lacking this gene. This dose is equivalent to human dose of 100-200 mg/day. If this dosage is not effective, additional ranges may be contemplated, including, but not limited to 150-300 mg/day. In addition, due to the inducibility of the pTet-CMV-TGF-β1, expression of the vector can be "turned on and off" by administering doxycycline when expression is desired.

The methods and compositions of the present invention are not limited to the treatment of IBD. Indeed, it is contemplated that the methods and compositions of the present invention will find use in the treatment of various other diseases. In particular, it is contemplated that the present invention will find use in the treatment of various diseases with an autoimmune component. Diseases contemplated include, but are not limited to, multiple sclerosis, rheumatoid arthritis, systemic lupus erythematosus, insulin-dependent diabetes mellitus, sarcoidosis, and psoriasis.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention should not be unduly limited to such specific embodiments. Indeed, various modifications of the described modes for carrying out the invention which are obvious to those skilled in medicine, pharmacology, histology, diagnostics, and molecular biology or related fields are intended to be within the scope of the following claims.

We claim:

1. A vector comprising i) a nucleic acid sequence encoding tetracycline controlled transactivator (tTA) under the control of a CMV promoter, and ii) the nucleic acid sequence of SEQ ID NO: 1 operably linked to an inducible tetracycline responsive element-cytomegalovirus (TRE-CMV) promoter, wherein the CMV and TRE-CMV promoters are placed in opposite orientation.

2. A composition comprising a cell which contains the vector of claim 1.

3. A vector comprising i) a nucleic acid sequence encoding tetracycline controlled transactivator (tTA) under the control of a CMV promoter, and ii) the nucleic acid sequence encoding transforming growth factor-β (TGF-β) operably linked to an inducible tetracycline responsive element-cytomegalovirus (TRE-CMV) promoter, wherein the CMV and TRE-CMV promoters are placed in opposite orientation.

4. The vector of claim 3, wherein the TGF-β is selected from the group consisting of TGF-β1, TGF-β2, TGF-β3, variants of TGF-β1, variants of TGF-β2, variants of TGF-β3, homologs of TGF-β1, homologs of TGF-β2, and homologs of TGF-β3.

5. A host cell comprising the vector of claim 3.

6. A host cell comprising the vector of claim 4.

7. A host cell comprising the vector of claim 1.

8. The vector of claims 1 or 3, wherein the CMV and TRE-CMV promoters are both flanked by an SV40 late polyA sequence.

* * * * *

SEQUENCE LISTING

<160> NUMBER OF SEQ ID NOS: 6

<210> SEQ ID NO 1
<211> LENGTH: 1326
<212> TYPE: DNA
<213> ORGANISM: Sus scrofa
<220> FEATURE:
<221> NAME/KEY: CDS
<222> LOCATION: (16)..(1185)

<400> SEQUENCE: 1

```
agatctggta ccgag atg gcg cct tcg ggg ctg cgg ctc ttg ccg ctg ctg        51
              Met Ala Pro Ser Gly Leu Arg Leu Leu Pro Leu Leu
                1               5                  10 ctg ccg ctg ctg tgg ctg cta gtg ctg acg cct ggc cgg ccg gcc gcc        99
Leu Pro Leu Leu Trp Leu Leu Val Leu Thr Pro Gly Arg Pro Ala Ala
        15                  20                  25 gga ctg tcc acc tgc aag acc atc gac atg gag ctg gtg aag cgg aag       147
Gly Leu Ser Thr Cys Lys Thr Ile Asp Met Glu Leu Val Lys Arg Lys
    30                  35                  40 cgc atc gag gcc att cgc ggc cag att ctg tcc aag ctt cgg ctc gcc       195
Arg Ile Glu Ala Ile Arg Gly Gln Ile Leu Ser Lys Leu Arg Leu Ala
 45                  50                  55                  60 agc ccc ccg agc cag ggg gac gtg ccc ccc ggc ccg ctg cct gag gcc       243
Ser Pro Pro Ser Gln Gly Asp Val Pro Pro Gly Pro Leu Pro Glu Ala
                65                  70                  75 gta ctg gct ctt tac aac agt acc cgc gac cgg gta gcc ggg gaa agt       291
Val Leu Ala Leu Tyr Asn Ser Thr Arg Asp Arg Val Ala Gly Glu Ser
             80                  85                  90 gtc gaa ccg gag ccc gag cca gag gcg gac tac tac gcc aag gag gtc       339
Val Glu Pro Glu Pro Glu Pro Glu Ala Asp Tyr Tyr Ala Lys Glu Val
         95                 100                 105 acc cgc gtg cta atg gtg gaa agc ggc aac caa atc tat gat aaa ttc       387
Thr Arg Val Leu Met Val Glu Ser Gly Asn Gln Ile Tyr Asp Lys Phe
    110                 115                 120 aag ggc acc ccc cac agc tta tat atg ctg ttc aac acg tcg gag ctc       435
Lys Gly Thr Pro His Ser Leu Tyr Met Leu Phe Asn Thr Ser Glu Leu
125                 130                 135                 140 cgg gaa gcg gtg ccg gaa cct gta ttg ctc tct cgg gca gag ctg cgc       483
Arg Glu Ala Val Pro Glu Pro Val Leu Leu Ser Arg Ala Glu Leu Arg
                145                 150                 155 ctg ctg agg ctc aag tta aaa gtg gag cag cac gtg gag cta tac cag       531
Leu Leu Arg Leu Lys Leu Lys Val Glu Gln His Val Glu Leu Tyr Gln
            160                 165                 170 aaa tac agc aat gat tcc tgg cgc tac ctc agc aac cgg ctg ctg gcc       579
Lys Tyr Ser Asn Asp Ser Trp Arg Tyr Leu Ser Asn Arg Leu Leu Ala
        175                 180                 185 ccc agt gac tca ccg gag tgg ctg tcc ttt gat gtc acc gga gtt gtg       627
Pro Ser Asp Ser Pro Glu Trp Leu Ser Phe Asp Val Thr Gly Val Val
    190                 195                 200 cgg cag tgg ctg acc cgc aga gag gct ata gag ggt ttt cgc ctc agt       675
Arg Gln Trp Leu Thr Arg Arg Glu Ala Ile Glu Gly Phe Arg Leu Ser
205                 210                 215                 220 gcc cac tct tcc tct gac agc aaa gat aac aca ctc cac gtg gaa att       723
Ala His Ser Ser Ser Asp Ser Lys Asp Asn Thr Leu His Val Glu Ile
                225                 230                 235 aac ggg ttc aat tct ggc cgc cgg ggt gac ctg gcc acc att cac ggc       771
Asn Gly Phe Asn Ser Gly Arg Arg Gly Asp Leu Ala Thr Ile His Gly
            240                 245                 250
```

```
atg aac cgg ccc ttc ctg ctc ctc atg gcc acc ccg ctg gag agg gcc      819
Met Asn Arg Pro Phe Leu Leu Leu Met Ala Thr Pro Leu Glu Arg Ala
    255                 260                 265 cag cac ctg cac agc tcc cgg cac cgc cga gcc ctg gat acc aac tac      867
Gln His Leu His Ser Ser Arg His Arg Arg Ala Leu Asp Thr Asn Tyr
270                 275                 280 tgc ttc agc tcc acg gag aag aac tgc tgc gtg cgg cag ctc tac att      915
Cys Phe Ser Ser Thr Glu Lys Asn Cys Cys Val Arg Gln Leu Tyr Ile
285                 290                 295                 300 gac ttc cgg aag gac ctg ggc tgg aag tgg att cat gaa ccc aag ggc      963
Asp Phe Arg Lys Asp Leu Gly Trp Lys Trp Ile His Glu Pro Lys Gly
            305                 310                 315 tac cat gcc aat ttc tgc ctg ggg ccc tgt ccc tac atc tgg agc cta     1011
Tyr His Ala Asn Phe Cys Leu Gly Pro Cys Pro Tyr Ile Trp Ser Leu
        320                 325                 330 gac act cag tac agc aag gtc ctg gct ctg tac aac cag cac aac ccg     1059
Asp Thr Gln Tyr Ser Lys Val Leu Ala Leu Tyr Asn Gln His Asn Pro
    335                 340                 345 ggc gcg tcg gcg gcg ccg tgc tgc gtg ccg cag gcg ctg gag cca ctg     1107
Gly Ala Ser Ala Ala Pro Cys Cys Val Pro Gln Ala Leu Glu Pro Leu
350                 355                 360 ccc atc gtg tac tac gtg ggc cgc aag ccc aag gtg gag cag ctg tcc     1155
Pro Ile Val Tyr Tyr Val Gly Arg Lys Pro Lys Val Glu Gln Leu Ser
365                 370                 375                 380 aac atg atc gtg cgt tcc tgc aag tgc agc tgagccccgc cccgcccaca       1205
Asn Met Ile Val Arg Ser Cys Lys Cys Ser
            385                 390 gccccgccca ccggcaggc ccggccccac ccccgcccgc tcaccgggg ctgtatttaa     1265 ggacatcgtg ccccaagccc actgggatcg attaaaggtg gagagaggag gtaccagatc  1325
t                                                                 1326

<210> SEQ ID NO 2
<211> LENGTH: 390
<212> TYPE: PRT
<213> ORGANISM: Sus scrofa

<400> SEQUENCE: 2

Met Ala Pro Ser Gly Leu Arg Leu Leu Pro Leu Leu Pro Leu Leu
1               5                   10                  15

Trp Leu Leu Val Leu Thr Pro Gly Arg Pro Ala Ala Gly Leu Ser Thr
                20                  25                  30

Cys Lys Thr Ile Asp Met Glu Leu Val Lys Arg Lys Arg Ile Glu Ala
            35                  40                  45

Ile Arg Gly Gln Ile Leu Ser Lys Leu Arg Leu Ala Ser Pro Pro Ser
        50                  55                  60

Gln Gly Asp Val Pro Pro Gly Pro Leu Pro Glu Ala Val Leu Ala Leu
65                  70                  75                  80

Tyr Asn Ser Thr Arg Asp Arg Val Ala Gly Glu Ser Val Glu Pro Glu
                85                  90                  95

Pro Glu Pro Glu Ala Asp Tyr Tyr Ala Lys Glu Val Thr Arg Val Leu
            100                 105                 110

Met Val Glu Ser Gly Asn Gln Ile Tyr Asp Lys Phe Lys Gly Thr Pro
        115                 120                 125

His Ser Leu Tyr Met Leu Phe Asn Thr Ser Glu Leu Arg Glu Ala Val
    130                 135                 140

Pro Glu Pro Val Leu Leu Ser Arg Ala Glu Leu Arg Leu Leu Arg Leu
145                 150                 155                 160
```

Lys Leu Lys Val Glu Gln His Val Glu Leu Tyr Gln Lys Tyr Ser Asn
                165                 170                 175

Asp Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
        195                 200                 205

Thr Arg Arg Glu Ala Ile Glu Gly Phe Arg Leu Ser Ala His Ser Ser
    210                 215                 220

Ser Asp Ser Lys Asp Asn Thr Leu His Val Glu Ile Asn Gly Phe Asn
225                 230                 235                 240

Ser Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu His
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
    290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
    370                 375                 380

Arg Ser Cys Lys Cys Ser
385                 390

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
agaagttggt cgtgaggcac tg                                              22

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gagctccgac gtgttgaaca g                                               21

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic

```
                                    -continued
      primer

<400> SEQUENCE: 5
gtcttcacca ccatggagaa ggct                                              24

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
catgccagtg agcttcccgt tca                                               23
```